(12) United States Patent     (10) Patent No.: US 7,621,270 B2
Morris et al.     (45) Date of Patent: *Nov. 24, 2009

(54) SYSTEM AND METHOD FOR PROVIDING A BREATHING GAS

(75) Inventors: Make Morris, Shreveport, LA (US); Gregory William Flolid, North Royalton, OH (US); Neal Joseph Curran, Lakewood, OH (US)

(73) Assignee: Invacare Corp., Elyria, OH (US)

( * ) Notice: Subject to any disclaimer, the term of this patent is extended or adjusted under 35 U.S.C. 154(b) by 791 days.

This patent is subject to a terminal disclaimer.

(21) Appl. No.: 11/157,089

(22) Filed: Jun. 20, 2005

(65) Prior Publication Data

US 2005/0268913 A1     Dec. 8, 2005

Related U.S. Application Data

(63) Continuation-in-part of application No. 10/601,720, filed on Jun. 23, 2003, now Pat. No. 7,152,598.

(60) Provisional application No. 60/580,845, filed on Jun. 18, 2004.

(51) Int. Cl.
*A61M 16/00*     (2006.01)

(52) U.S. Cl. .............................. 128/204.23; 128/204.18; 128/204.21

(58) Field of Classification Search ............ 128/204.18, 128/204.21, 204.23, 205.23, 205.24, 205.18, 128/200.24, 204.22

See application file for complete search history.

(56) References Cited

U.S. PATENT DOCUMENTS 3,921,628 A    11/1975   Smythe et al.

4,011,859 A    3/1977   Frankenberger (Continued)

FOREIGN PATENT DOCUMENTS

WO     02/26287 A2     4/2002

(Continued)

OTHER PUBLICATIONS

Int'l App. No. PCT/US01/30768, International Preliminary Examination Report, 5 pages, report completed Apr. 15, 2003.

(Continued)

*Primary Examiner*—Steven O Douglas
(74) *Attorney, Agent, or Firm*—Calfee, Halter & Griswold LLP

(57) ABSTRACT

Systems and methods for providing a breathing gas are provided. In one embodiment, the method includes sensing a sensed parameter associated with delivery of the breathing gas, changing a control parameter associated with a flow/pressure control element in response to a difference between the sensed parameter and a first predetermined sensed parameter value during a first portion of a breathing cycle, determining a transition from the first portion to a second portion of the breathing cycle based at least in part on the changing control parameter, changing the control parameter to cause a first change in the sensed parameter during the second portion of the breathing cycle based at least in part on the determined transition, and changing the control parameter to cause a second change in the sensed parameter during a third portion of the breathing cycle based at least in part on the first predetermined sensed parameter value.

67 Claims, 10 Drawing Sheets

U.S. PATENT DOCUMENTS

| | | |
|---|---|---|
| 4,121,578 A | 10/1978 | Torzala |
| 4,350,166 A | 9/1982 | Mobarry |
| 4,506,678 A | 3/1985 | Russell et al. |
| 4,648,396 A | 3/1987 | Raemer |
| 4,651,729 A | 3/1987 | Rae |
| 4,655,213 A | 4/1987 | Rapoport et al. |
| 4,713,558 A | 12/1987 | Russell et al. |
| 4,728,499 A | 3/1988 | Fehder |
| 4,773,411 A | 9/1988 | Downs |
| 4,817,013 A | 3/1989 | Corenman et al. |
| 4,821,736 A | 4/1989 | Watson |
| 4,944,310 A | 7/1990 | Sullivan |
| 4,994,117 A | 2/1991 | Fehder |
| 5,044,362 A | 9/1991 | Younes |
| 5,065,756 A | 11/1991 | Rapoport |
| 5,094,235 A | 3/1992 | Westenskow et al. |
| 5,117,819 A | 6/1992 | Servidio et al. |
| 5,124,129 A | 6/1992 | Riccitelli et al. |
| 5,134,995 A | 8/1992 | Gruenke et al. |
| 5,148,802 A | 9/1992 | Sanders et al. |
| 5,166,075 A | 11/1992 | Fehder |
| 5,179,002 A | 1/1993 | Fehder |
| 5,193,544 A | 3/1993 | Jaffe |
| 5,199,424 A | 4/1993 | Sullivan et al. |
| 5,203,343 A | 4/1993 | Axe et al. |
| 5,239,995 A | 8/1993 | Estes et al. |
| 5,245,995 A | 9/1993 | Sullivan et al. |
| 5,251,632 A | 10/1993 | Delpy |
| 5,279,289 A | 1/1994 | Kirk |
| 5,313,937 A | 5/1994 | Zdrojkowski |
| 5,332,901 A | 7/1994 | Eckles et al. |
| 5,335,650 A | 8/1994 | Shaffer et al. |
| 5,335,654 A | 8/1994 | Rapoport |
| 5,343,878 A | 9/1994 | Scarberry et al. |
| 5,353,788 A | 10/1994 | Miles |
| 5,394,882 A | 3/1995 | Mawhinney |
| 5,433,193 A | 7/1995 | Sanders et al. |
| 5,438,980 A | 8/1995 | Phillips |
| 5,445,160 A | 8/1995 | Culver et al. |
| 5,456,249 A | 10/1995 | Kirk |
| 5,458,137 A | 10/1995 | Axe et al. |
| 5,490,502 A | 2/1996 | Rapoport et al. |
| 5,492,113 A | 2/1996 | Estes et al. |
| 5,503,146 A | 4/1996 | Froehlich et al. |
| 5,522,382 A | 6/1996 | Sullivan et al. |
| RE35,295 E | 7/1996 | Estes et al. |
| 5,535,738 A | 7/1996 | Estes et al. |
| 5,535,739 A | 7/1996 | Rapoport et al. |
| 5,537,997 A | 7/1996 | Mechlenburg et al. |
| 5,538,000 A | 7/1996 | Rudolph |
| 5,540,219 A | 7/1996 | Mechlenburg et al. |
| 5,546,933 A | 8/1996 | Rapoport et al. |
| 5,549,106 A | 8/1996 | Gruenke et al. |
| 5,551,418 A | 9/1996 | Estes et al. |
| 5,551,419 A | 9/1996 | Froehlich et al. |
| 5,558,638 A | 9/1996 | Evers et al. |
| RE35,339 E | 10/1996 | Rapoport |
| 5,592,938 A | 1/1997 | Scarberry et al. |
| 5,598,838 A | 2/1997 | Servidio et al. |
| 5,630,411 A | 5/1997 | Holscher |
| 5,632,269 A | 5/1997 | Zdrojkowski |
| 5,645,054 A | 7/1997 | Cotner et al. |
| 5,655,522 A | 8/1997 | Mechlenburg et al. |
| 5,679,884 A | 10/1997 | Kirk |
| 5,682,878 A | 11/1997 | Ogden |
| 5,694,923 A | 12/1997 | Hete et al. |
| 5,701,883 A | 12/1997 | Hete et al. |
| 5,704,345 A | 1/1998 | Berthon-Jones |
| 5,715,812 A | 2/1998 | Deighan et al. |
| 5,738,106 A | 4/1998 | Yamamori et al. |
| 5,740,795 A | 4/1998 | Brydon |
| 5,765,563 A | 6/1998 | Vander Schaaf |
| 5,794,614 A | 8/1998 | Gruenke et al. |
| 5,794,615 A | 8/1998 | Estes |
| 5,803,065 A | 9/1998 | Zdrojkowski et al. |
| 5,803,066 A | 9/1998 | Rapoport et al. |
| 5,823,187 A | 10/1998 | Estes et al. |
| 5,845,636 A | 12/1998 | Gruenke et al. |
| 5,865,173 A | 2/1999 | Froehlich |
| 5,881,717 A | 3/1999 | Isaza |
| 5,881,723 A | 3/1999 | Wallace et al. |
| 5,901,704 A | 5/1999 | Estes et al. |
| 5,904,141 A | 5/1999 | Estes et al. |
| 5,915,379 A | 6/1999 | Wallace et al. |
| 5,915,380 A | 6/1999 | Wallace et al. |
| 5,927,274 A | 7/1999 | Servidio et al. |
| 5,937,851 A | 8/1999 | Serowski et al. |
| 5,947,115 A | 9/1999 | Lordo et al. |
| 5,953,713 A | 9/1999 | Behbehani et al. |
| 5,954,050 A | 9/1999 | Christopher |
| 5,970,975 A | 10/1999 | Estes et al. |
| 6,017,315 A | 1/2000 | Starr et al. |
| 6,024,089 A | 2/2000 | Wallace et al. |
| 6,026,312 A | 2/2000 | Shemwell et al. |
| 6,029,660 A | 2/2000 | Calluaud et al. |
| 6,029,664 A | 2/2000 | Zdrojkowski et al. |
| 6,029,665 A | 2/2000 | Berthon-Jones |
| 6,044,843 A | 4/2000 | O'Neil et al. |
| 6,071,237 A | 6/2000 | Weil et al. |
| 6,085,747 A | 7/2000 | Axe et al. |
| 6,091,973 A | 7/2000 | Colla et al. |
| 6,095,974 A | 8/2000 | Shemwell et al. |
| 6,099,481 A | 8/2000 | Daniels et al. |
| 6,102,042 A | 8/2000 | Hete et al. |
| 6,105,575 A | 8/2000 | Estes et al. |
| 6,123,074 A | 9/2000 | Hete et al. |
| 6,123,075 A | 9/2000 | Kirk |
| 6,135,106 A | 10/2000 | Dirks et al. |
| 6,138,675 A | 10/2000 | Berthon-Jones |
| 6,142,952 A | 11/2000 | Behbehani et al. |
| 6,152,129 A | 11/2000 | Berthon-Jones |
| 6,155,257 A | 12/2000 | Lurie et al. |
| 6,155,986 A | 12/2000 | Brydon et al. |
| 6,182,657 B1 | 2/2001 | Brydon et al. |
| 6,183,423 B1 | 2/2001 | Gaumond et al. |
| 6,212,435 B1 | 4/2001 | Lattner et al. |
| 6,213,119 B1 | 4/2001 | Brydon et al. |
| 6,237,592 B1 | 5/2001 | Surjadi et al. |
| 6,237,593 B1 | 5/2001 | Brydon |
| 6,240,921 B1 | 6/2001 | Brydon et al. |
| 6,253,764 B1 | 7/2001 | Calluaud |
| 6,257,234 B1 | 7/2001 | Sun |
| 6,269,811 B1 | 8/2001 | Duff et al. |
| 6,269,812 B1 | 8/2001 | Wallace et al. |
| 6,279,569 B1 | 8/2001 | Berthon-Jones |
| 6,286,508 B1 | 9/2001 | Remmers et al. |
| 6,299,581 B1 | 10/2001 | Rapoport et al. |
| 6,302,105 B1 | 10/2001 | Wickham et al. |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,347,631 B1 | 2/2002 | Hansen et al. |
| 6,349,724 B1 | 2/2002 | Burton et al. |
| 6,357,463 B1 | 3/2002 | Wickham et al. |
| 6,367,474 B1 | 4/2002 | Berthon-Jones et al. |
| 6,443,154 B1 | 9/2002 | Jalde et al. |
| 6,467,477 B1 | 10/2002 | Frank et al. |
| 6,609,517 B1 | 8/2003 | Estes et al. |
| 6,636,021 B2 | 10/2003 | Schenkel et al. |
| 6,745,770 B2 | 6/2004 | McAuliffe et al. |
| 6,752,151 B2 | 6/2004 | Hill |
| 6,766,800 B2 | 7/2004 | Chu et al. |
| 6,796,305 B1 | 9/2004 | Banner et al. |
| 6,817,361 B2 | 11/2004 | Berthon-Jones et al. |

| | | |
|---|---|---|
| 6,823,866 B2 | 11/2004 | Jafari et al. |
| 6,866,040 B1 | 3/2005 | Bourdon |
| 6,895,964 B2 | 5/2005 | McAuliffe et al. |
| 6,932,084 B2 | 8/2005 | Estes et al. |
| 6,968,842 B1 | 11/2005 | Truschel et al. |
| 7,066,173 B2 | 6/2006 | Banner et al. |
| 7,089,936 B2 | 8/2006 | Madaus et al. |
| 7,152,598 B2 * | 12/2006 | Morris et al. .......... 128/204.23 |
| 7,168,429 B2 | 1/2007 | Matthews et al. |
| 2001/0004894 A1 | 6/2001 | Bourdon |
| 2001/0015204 A1 | 8/2001 | Hansen et al. |
| 2001/0027791 A1 | 10/2001 | Wallace et al. |
| 2001/0027792 A1 | 10/2001 | Berthon-Jones et al. |
| 2001/0035186 A1 | 11/2001 | Hill |
| 2001/0035187 A1 | 11/2001 | Smith et al. |
| 2002/0104536 A1 | 8/2002 | Richey, II |
| 2003/0159695 A1 | 8/2003 | Younes |
| 2004/0035422 A1 | 2/2004 | Truitt et al. |
| 2004/0103896 A1 | 6/2004 | Jafari et al. |
| 2004/0107953 A1 | 6/2004 | Hegge et al. |
| 2004/0123866 A1 | 7/2004 | Berthon-Jones |
| 2004/0187870 A1 | 9/2004 | Matthews et al. |
| 2005/0016536 A1 | 1/2005 | Rapoport et al. |
| 2005/0020932 A1 | 1/2005 | Haberland et al. |
| 2005/0034724 A1 | 2/2005 | O'Dea |
| 2005/0080461 A1 | 4/2005 | Stahmann et al. |
| 2005/0166922 A1 | 8/2005 | Knepper |
| 2005/0224078 A1 | 10/2005 | Zdrojkowski et al. |
| 2005/0241639 A1 | 11/2005 | Zilberg |
| 2006/0000475 A1 | 1/2006 | Matthews et al. |
| 2006/0011200 A1 | 1/2006 | Remmers et al. |
| 2006/0162728 A1 | 7/2006 | Delache et al. |
| 2007/0000494 A1 | 1/2007 | Banner et al. |
| 2007/0016093 A1 | 1/2007 | Rapoport et al. |
| 2007/0028921 A1 | 2/2007 | Banner et al. |
| 2007/0051371 A1 | 3/2007 | Sullivan et al. |
| 2007/0167843 A1 | 7/2007 | Cho et al. |

FOREIGN PATENT DOCUMENTS

WO 2005/028009 A1 3/2005

OTHER PUBLICATIONS

Int'l App. No. PCT/US01/30768, International Search Report, 3 pages, mailed May 31, 2002.
Int'l App. No. PCT/US01/30768, Written Opinion of the International Preliminary Examining Authority, 5 pages, mailed Dec. 12, 2002.
Int'l App. No. PCT/US04/007170, International Preliminary Report on Patentability, 5 pages, report completed Sep. 8, 2005.
Int'l App. No. PCT/US04/007170, International Search Report, 2 pages, mailed Jan. 27, 2005.
Int'l App. No. PCT/US04/007170, Written Opinion of the International Searching Authority, 5 pages, mailed Jan. 27, 2005.
U.S. Appl. No. 09/967,274, Final Office Action, 7 pages, mailed Jan. 25, 2005.
U.S. Appl. No. 09/967,274, Non-final Office Action, 6 pages, mailed Jul. 27, 2004.
U.S. Appl. No. 09/967,274, Non-final Office Action, 8 pages, mailed Apr. 23, 2003.
U.S. Appl. No. 09/967,274, Non-final Office Action, 8 pages, mailed Jan. 14, 2004.
U.S. Appl. No. 09/967,274, Notice of Allowance and Fee(s) Due and Notice of Allowability with Examiner's Statement of Reasons for Allowance, 6 pages, mailed Jul. 11, 2005.
U.S. Appl. No. 10/601,720, Non-final Office Action, 6 pages, mailed Jun. 21, 2005.
U.S. Appl. No. 10/601,720, Non-final Office Action, 7 pages, mailed Jan. 6, 2005.
U.S. Appl. No. 10/601,720, Non-final Office Action, 8 pages, mailed Feb. 7, 2006.
U.S. Appl. No. 10/601,720, Notice of Allowance and Fee(s) Due and Notice of Allowability, 4 pages, mailed Aug. 8, 2006.
Belozeroff et al., Effects of CPAP therapy on cardiovascular variability in obstructive sleep apnea: a closed-loop analysis, Am J Physiol—Heart Circ Physiol, vol. 282, pp. H110-H121, Jan. 2002.
Bliss et al., Performance of Auto-Titrating CPAP Devices in a Simulation of Varied Patient Breathing, AARC International Congress, San Antonio, TX, 6 pages, Dec. 2001.
Cairo et al., Mosby's Respiratory Care Equipment, Chapter 14—Sleep Diagnostics, pp. 682-698, 7th ed., Jul. 31, 2003.
Farre et al., Response of Automatic Continuous Positive Airway Pressure Devices to Different Sleep Breathing Patterns—A Bench Study, Am J Respir Crit Care Med, vol. 166, pp. 469-473, 2002.
Heitman et al., Validation of Nasal Pressure for the Identification of Apneas/Hypopneas during Sleep, Am J Respir Crit Care Med, vol. 166, pp. 386-391, 2002.
Invacare Corp., Owner's Manual, Polaris/Polaris LT Nasal CPAP System, 20 pages, Copyright 2002, Ref F—Jul. 2002.
Lankford, Got Compliance?, ResMed PowerPoint presentation, 34 pages.
Leung et al., Sleep Apnea and Cardiovascular Disease, Am J Respir Crit Care Med, vol. 164, pp. 2147-2165, 2001.
Liesching et al., Evaluation of the Accuracy of SNAP Technology Sleep Sonography in Detecting Obstructive Sleep Apnea in Adults Compared to Standard Polysomnography, Chest—the Cardiopulmonary and Critical Care Journal, vol. 125, No. 3, pp. 886-891, Mar. 2004.
Mallinckrodt, Inc., Break free to Breeze and DreamSeal, Puritan-Bennett SleepGear, MS-AC/Breeze/GB, 6 pages, Copyright 2000.
Penzel et al., Systemic comparison of different algorithms for apnoea detection based on electrocardiogram recordings, Medical & Biological Engineering & Computing, vol. 40, pp. 402-407, 2002.
Portier et al., Evaluation of Home versus Laboratory Polysomnography in the Diagnosis of Sleep Apnea Syndrome, Am J Respir Crit Care Med, vol. 162, pp. 814-818, 2000.
Ryan et al., Periodicity of Obstructive Sleep Apnea in Patients With and Without Heart Failure, Chest Journal, vol. 127, No. 2, pp. 536-542, Feb. 2005.
Tamisier et al., Expiratory Changes in Pressure: Flow Ratio During Sleep in Patients with Sleep-disordered Breathing, Sleep, vol. 27, No. 2, pp. 240-248, 2004.
Tyco Healthcare UK Ltd., Breeze SleepGear CPAP Interface System, A.b. 1751-0504, ST00900, 2 pages, Copyright 2004.
Tyco Healthcare UK Ltd., Breeze SleepGear CPAP Interface System, C-AD-Breeze/GB, 4 pages, Copyright 2004, Jul. 2004.
U.S. Appl. No. 11/206,410, Non-final Office Action, 10 pages, mailed May 28, 2008.

* cited by examiner

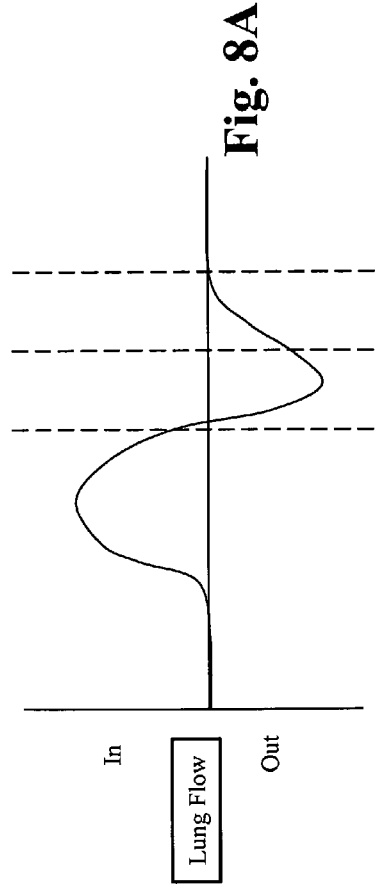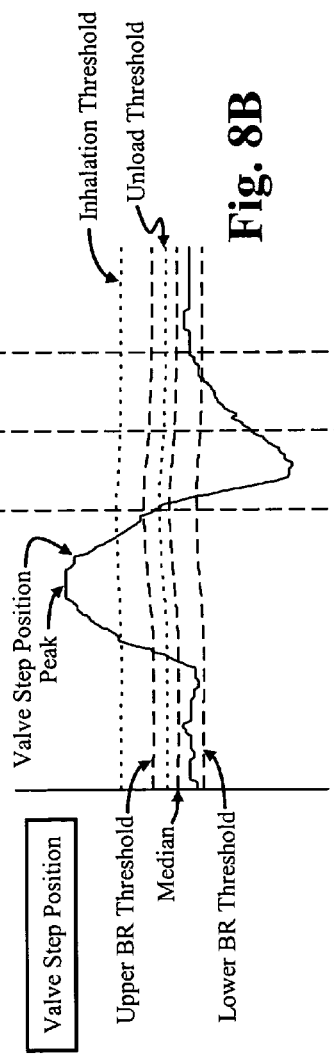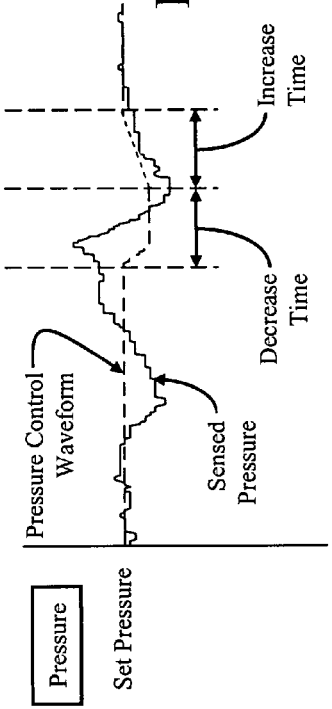

SYSTEM AND METHOD FOR PROVIDING A BREATHING GAS

This is a continuation-in-part (CIP) of U.S. patent application Ser. No. 10/601,720, filed Jun. 23, 2003, now U.S. Pat. No. 7,152,598 and also claims priority to U.S. provisional patent application Ser. No. 60/580,845, filed Jun. 18, 2004.

FIELD OF THE INVENTION

The invention relates generally to the delivery of a breathing gas to an airway of a patient, and more particularly, to the delivery of a breathing gas coordinated with the breathing cycle of the patient.

BACKGROUND

Obstructive sleep apnea is an airway breathing disorder caused by relaxation of the muscles of the upper airway to the point where the upper airway collapses or becomes obstructed by these same muscles. It is known that obstructive sleep apnea can be treated through the application of pressurized air to the nasal passages of a patient. The application of pressurized air forms a pneumatic splint in the upper airway of the patient thereby preventing the collapse or obstruction thereof.

Within the treatment of obstructive sleep apnea, there are several known CPAP regimens including, for example, mono-level CPAP and bi-level CPAP. Mono-level CPAP involves the constant application of a single therapeutic or medically prescribed CPAP level. That is, through the entire breathing cycle, a single therapeutic positive air pressure is delivered to the patient. While such a regimen is successful in treating obstructive sleep apnea, some patients experience discomfort when exhaling because of the level of positive air pressure being delivered to their airways during exhalation.

In response to this discomfort, bi-level CPAP regimens were developed. Bi-level CPAP involves delivering a higher therapeutic CPAP during inhalation and a lower therapeutic CPAP during exhalation. The higher therapeutic CPAP level is commonly known as inspiratory positive airway pressure or "EPAP." The lower therapeutic CPAP level is commonly known as expiratory positive airway pressure or, "EPAP." Since the EPAP is lower than the IPAP, the patient needs to do less work during exhalation to exhale and thus experiences less discomfort, compared to the mono-level CPAP regimen.

However, the development of bi-level CPAP significantly increased the sophistication of CPAP devices because the devices must accurately determine when the patient is inhaling and exhaling and to properly coordinate the IPAP and EPAP levels thereto. One approach is to determine the instantaneous and average flow rates of air being delivered to the patient and then to compare the two to determine whether a patient was inhaling or exhaling. If the instantaneous flow rate is greater than the average flow rate, the patient is deemed to be inhaling. If the instantaneous flow rate is less than the average flow rate, the patient is deemed to be exhaling.

While CPAP has been useful in the treatment of obstructive sleep apnea and other respiratory related illnesses such as, for example, chronic obstructive pulmonary disease and neuro-muscular disorders affecting the muscles and tissues of breathing, it is highly desirable to provide additional ways of delivering a therapeutic breathing gas to a patient.

SUMMARY

In one aspect, a method of providing a breathing gas is provided. In one embodiment, the method includes: a) sensing a sensed parameter associated with delivery of the breathing gas, b) changing a control parameter associated with a flow/pressure control element in response to a difference between the sensed parameter and a first predetermined sensed parameter value during a first portion of a current breathing cycle, c) determining a transition from the first portion to a second portion of the current breathing cycle based at least in part on the changing control parameter, d) changing the control parameter to cause a first change in the sensed parameter during the second portion of the current breathing cycle based at least in part on the determined transition, and e) changing the control parameter to cause a second change in the sensed parameter during a third portion of the current breathing cycle based at least in part on the first predetermined sensed parameter value.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

FIGS. 8A-8C illustrate a lung flow, valve step position, control pressure and sensed pressure over time for the embodiment of the system illustrated in FIG. 6.

DETAILED DESCRIPTION OF ILLUSTRATED EMBODIMENTS

Prior to discussing the various embodiments, a review of the definitions of some exemplary terms used throughout the disclosure is appropriate. Both singular and plural forms of all terms fall within each meaning:

"Logic," as used herein, includes but is not limited to hardware, firmware, software and/or combinations of each to perform a function(s) or an action(s), and/or to cause a function or action from another component. For example, based on a desired application or need, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

"Breathing state," as used herein, includes any state or combination of states where air is drawn into the lungs and/or expelled from the lungs. For example, a first breathing state may be associated with drawing air into the lungs and a second breathing state may be associated with expelling air from the lungs. Additionally, a breathing state can have one or more sub-states. For example, the start of inhalation can be a breathing state and the end of inhalation can be another breathing state, with the range therebetween defining one or more other breathing states. Similarly, the start and end of exhalation, and the range there between, can also be defined by one or more breathing states.

Figure 1:
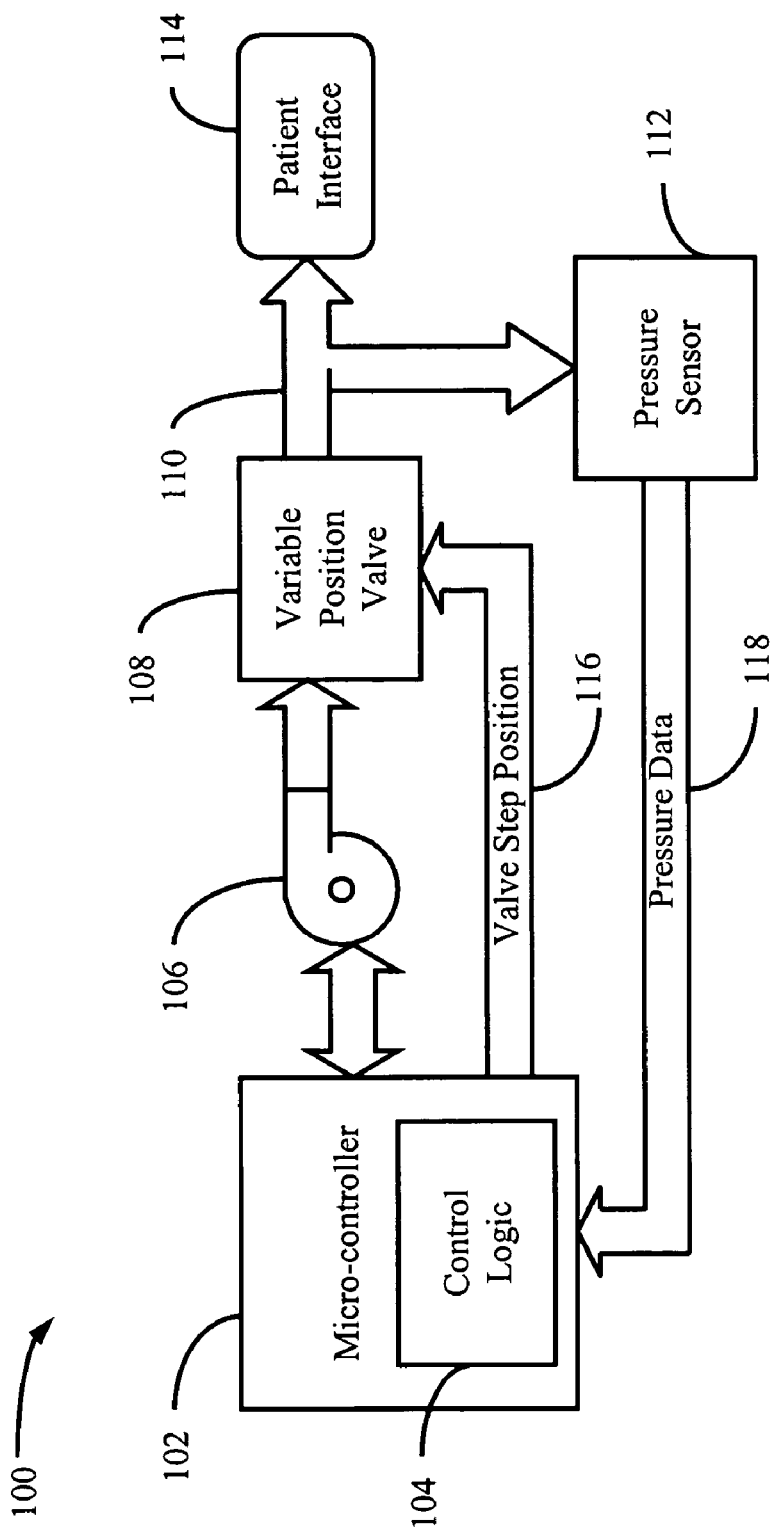
FIG. 1 is a functional block diagram illustrating one embodiment of a system for delivering a breathing gas.

The systems and methods described herein are particularly suited for assisting the respiration of spontaneously breathing patients, though they may also be applied to other respiratory regimens including, for example, acute and homecare ventilation. Referring now to FIG. 1, block diagram 100 illustrating one embodiment of a system is shown. The system has a controller 102 with control logic 104, a blower 106, a variable position poppet valve 108 with a bi-directional stepper motor and a pressure sensor 112. A flow path 110 provides a path for a flow of breathable gas from the valve 108 to a patient interface 114. Patent interface 114 can be any nasal mask, face mask, cannula, or similar device. Pressure sensor 112 senses a parameter of the breathing gas such as the pressure in flow path 110, which is associated with and indicative of the pressure in the patient interface 114. The controller 102 is preferably processor-based and can include various input/output circuitry including analog-to-digital (A/D) inputs and digital-to-analog (D/A) outputs. The controller 102 sends valve step position data 116 to the valve 108 to control its position and the sensor 112 sends pressure data 118 back to the controller 102 to be read.

The valve step position is preferably defined by the stepper motor specification and can include step positions that are less than 1 step or a whole step. Generally, the valve step position can range from any negative number to any positive number. One preferable valve step position range includes 0 to 100, where step position 0 is associated with a fully closed valve position and step 100 is associated with a fully open valve position. Therefore, for a given blower speed and valve configuration, each valve step position can be determined to be equivalent to an approximate pressure change (e.g., a valve step position equals a pressure change of 0.2 cm $H_2O$.)

While the embodiment of FIG. 1 has been described with reference to a flow/pressure control element in the form of a variable position valve 108 and a sensor element in the form of a pressure sensor 112, the flow/pressure control and sensor elements can include other types of devices. For example, the flow/pressure control element can be a variable speed blower, a variable speed blower in combination with a linear valve or solenoid valve, a variable speed blower in combination with a stepper motor controlled variable position valve, a variable speed blower in combination with a linear valve or solenoid valve and a stepper motor controlled variable position valve, or any other suitable combination of these components. The sensor element can include a flow sensor, temperature sensor, infra-red light emitter/sensor, motor current sensor, or motor speed sensor alone or in combination with the pressure sensor. The data generated from these sensor(s) is fed back to the controller 102 for processing.

Figure 2:
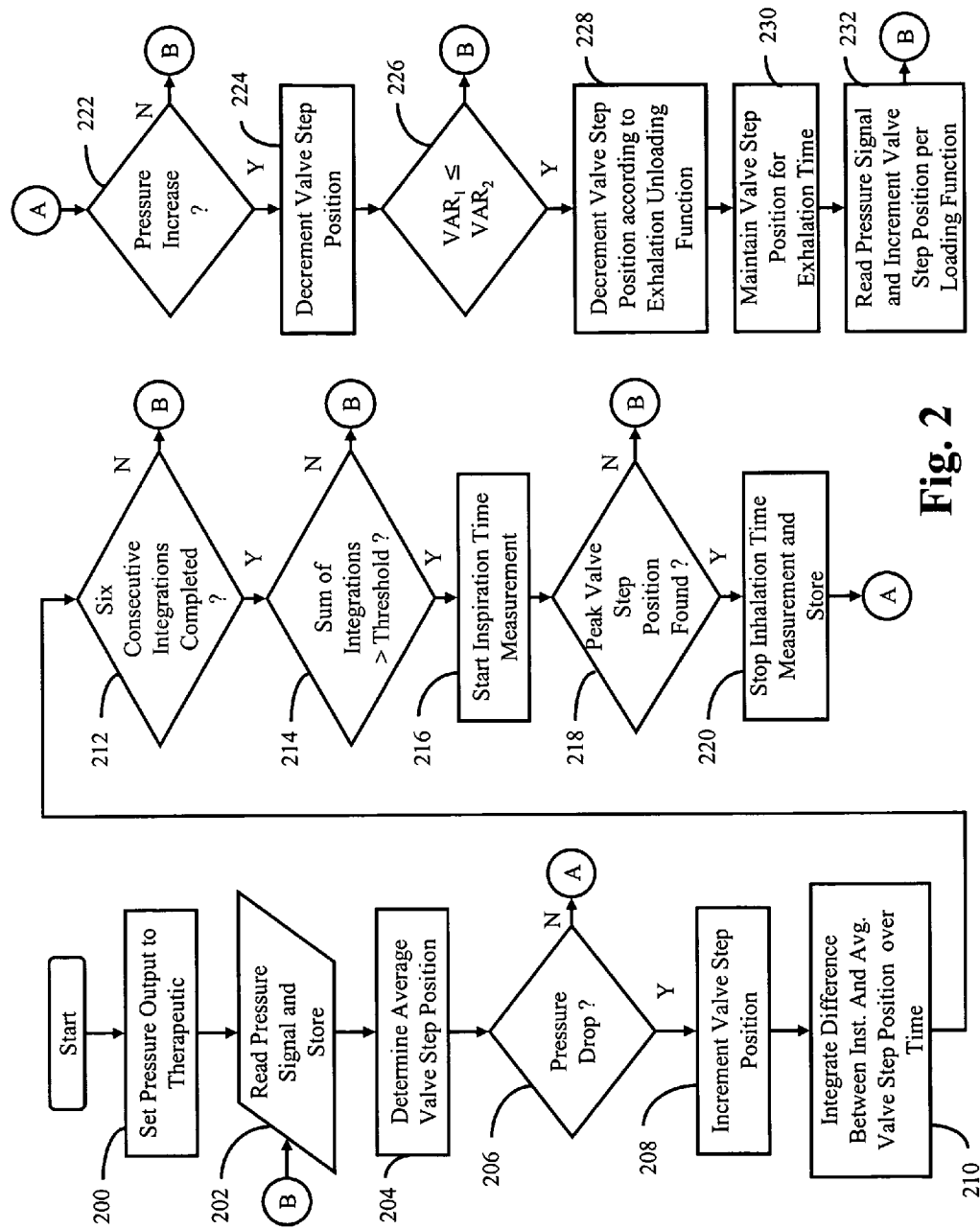
FIG. 2 is a flowchart illustrating one embodiment of a control process for the system.

Referring now to FIG. 2, the operation of the system will be described with reference to the flowchart illustrated therein. In the flowcharts hereinafter, the rectangular elements denote processing blocks and represent software instructions or groups of instructions. The quadrilateral elements denote data input/output processing blocks and represent software instructions or groups of instructions directed to the input or reading of data or the output or sending of data. The flow diagrams shown and described herein do not depict syntax of any particular programming language. Rather, the flow diagrams illustrate the functional information one skilled in the art may use to fabricate circuits or to generate software to perform the processing of the system. It should be noted that many routine program elements, such as initialization of loops and variables and the use of temporary variables are not shown.

In block 200, the controller 102 opens the valve 108 and sets the blower 106 to a speed that produces a predetermined pressure at its output. This predetermined pressure is generally set to a medically prescribed positive pressure for a patient plus an additional pressure of, for example, 5 cm $H_2O$, via a pressure-to-speed look-up table that is stored in the memory of the controller 102. While an additional pressure of 5 cm $H_2O$ has been described, other pressures including no additional pressure can be chosen as well. The medically prescribed positive pressure is typically a pressure that is above the ambient pressure. For example, the prescribed pressure may range from 4 to 20 cm $H_2O$. Once the blower 106 is set to provide the set pressure, it is rarely, if ever, changed during active operation of the device. Instead, the controller 102 uses the step position of the valve 108 to modulate the output pressure through both a closed loop and an open loop control. The closed loop control is a function of sensed pressure and the open loop control is a function of time. Together, these control loops direct the operation of the system through the breathing cycle of a patient. It should also be noted that the closed loop and open loop control can also be based on other parameters such as, for example, instantaneous and average flow rates, temperature of the gases in the patient interface, and/or composition of the gases (e.g. $CO_2$) in the patient interface.

In block 202, pressure is read and stored for subsequent processing. In block 204, an average valve step position is determined and maintained or updated. In step 206, the controller 102 determines if a pressure drop has been sensed. This is preferably accomplished by comparing the presently sensed pressure with the immediately preceding sensed pressure. If the presently sensed pressure is less, then a pressure drop has occurred and the flow proceeds to block 208. In block 208, the controller 102 increments the valve step position to compensate for the pressure drop. Incrementing the valve step position has the effect of increasing the flow and pressure of the breathing gas delivered from the valve's output. The step position is changed iteratively until the error or difference between the sensed pressures is minimized. During this phase of operation, the controller 102 seeks to maintain a constant pressure in the flow path 112 until patient exhalation is sensed.

In block 210, the difference between the instantaneous and average valve position is integrated over time and stored in memory. The summation of six such integrations is used to determine the start of an inhalation breathing state by determining if the summation is greater than a start of inhalation threshold (blocks 212 and 214). If the summation is greater than the threshold, the start of the inhalation breathing state has occurred and a timer begins the measurement of the inhalation breathing state in block 216. This measurement continues until a peak valve step position has been found in block 218. The peak valve step position is determined by comparing the previous valve step position to the present valve step position and saving in memory the step position that is greater as the peak valve step position. If the peak valve step position remains unchanged for some time period (e.g., 80 ms), then the controller 102 assumes that the peak valve step position has occurred for this inhalation phase and stops the inhalation breathing state time measurement in block 220. The peak valve step position is a threshold indicative of the imminent end of the inhalation breathing state.

In block 222, the controller 102 tests to determine if a pressure increase has occurred by reading the pressure signal. If a pressure increase has occurred after a peak valve step position has been found, then the inhalation breathing state is imminently ending. Block 224 decrements the valve position to lower the flow and pressure provided so as to maintain a constant pressure in the air flow path. This is once again accomplished by an iterative process by which the error between the presently sensed pressure and the previously sensed pressure is minimized. Block 226 tests to determine if the inhalation breathing state has ended by comparing two variables, $VAR_1$ and $VAR_2$. These variables are defined as follows:

$$VAR_1 = (\text{Inst. Step Position}) - (\text{Avg. Step Position})$$

$$VAR_2 = [(\text{Peak Step Position}) - (\text{Avg. Step Position})] * \text{Threshold}$$

The variable "Threshold" is a percentage value such as, for example, 85% or 0.85, though other percentage values can also be chosen. If $VAR_1 \leq VAR_2$, then the inhalation breathing state has ended and the exhalation breathing state has or is about to commence.

Block 228 decrements the valve step position according to an exhalation unloading function that lowers the pressure delivered over time so that the pressure initially delivered during the exhalation breathing state is less than the pressure delivered during the inhalation breathing state. The pressure is dropped until a predetermined minimum pressure is provided, which can include ambient pressure. This lower pressure is maintained in block 230 for an exhalation time period that is, for example, 2.5 times the measured inhalation state time period. Multiples other than 2.5 can also be selected after the expiration of this time period, the pressure signal is read in block 232 and the valve step position is incremented according to a pressure loading function. The pressure loading function reads the present pressure and returns over time the output pressure to the medically prescribed positive pressure, where the system once again looks for a start of inhalation breathing state.

In this manner, a positive pressure is provided during the inhalation phase of a breathing cycle to assist the patient in inhalation and a lower pressure is provided during the exhalation phase of a breathing cycle to allow the patient to exhale against a lower pressure. Such a system provides a level of comfort over other types of Continuous Positive Airway Pressure delivery in that the patient is not required to exhale against the same pressure used during inhalation for any appreciable period of time.

Figure 3:
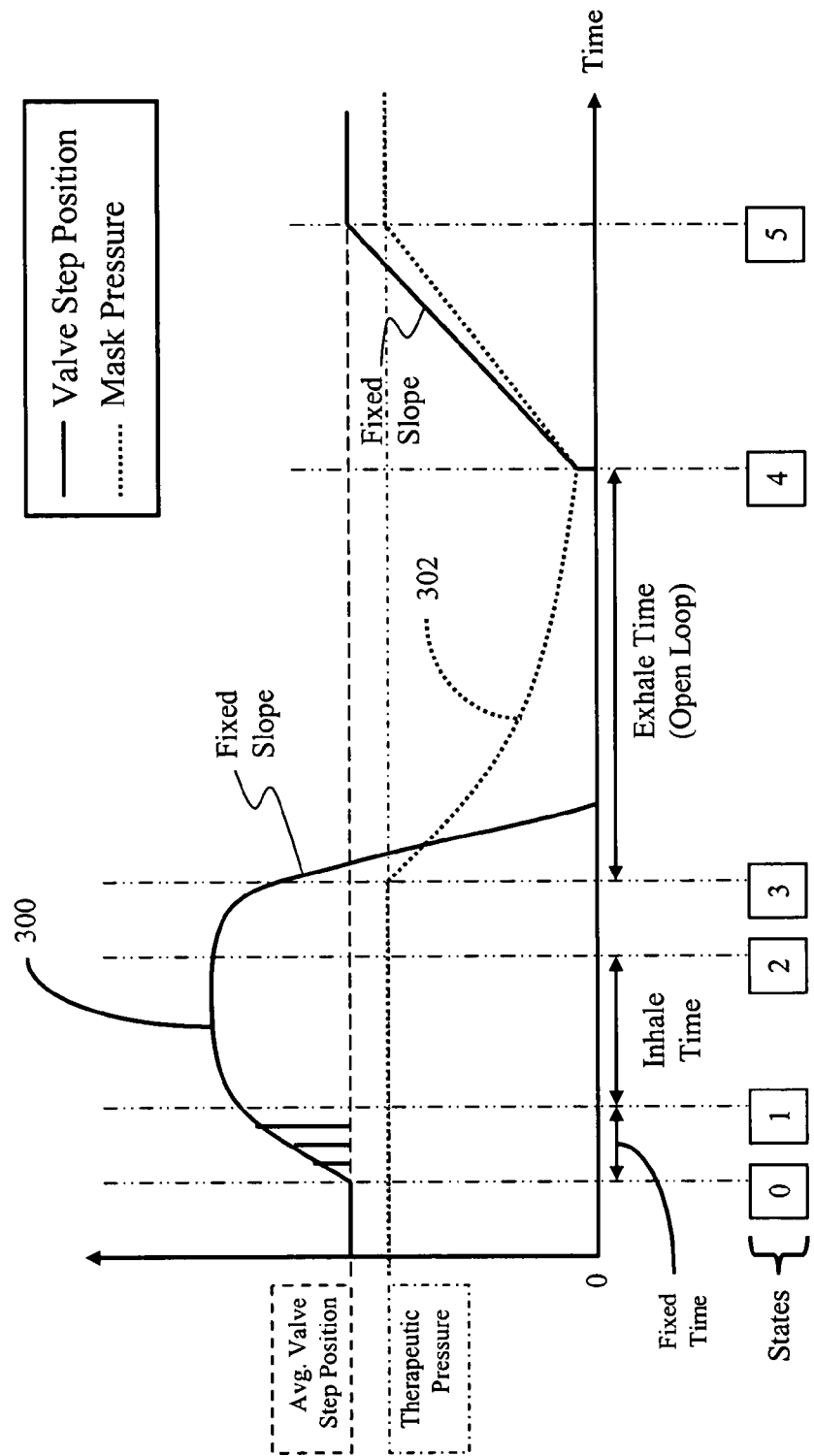
FIG. 3 is a graph illustrating a valve step position and mask pressure over time for one embodiment of the system.

Referring now to FIG. 3, a chart illustrating a valve step position curve 300 and an output pressure curve 302 as a function of time is shown. The two curves have been overlaid to more clearly illustrate the synchronization between pressure and valve step position. The operation description will now be reviewed with reference to the curves of FIG. 3.

Prior to state 0, the system is in the closed loop control and is sensing the pressure at its output via its pressure sensor. Since there is very little pressure change prior to state 0, the system is maintaining a constant valve step position, which results in a constant output pressure (preferably, the medically prescribed positive pressure). This typically occurs at the end of patient exhalation where there is very little pressure change in the system caused by the patient.

When the patient begins to inhale, a pressure drop is sensed by the pressure sensor 112. This pressure drop causes the system to further open the valve 108 in a step-wise fashion to compensate for the drop in pressure caused by patient inhalation. During such inhalation, the system attempts to maintain an output pressure substantially equivalent to the medically prescribed positive pressure. Each step position of the valve is equivalent to a known approximate pressure change (e.g., 0.2 cm $H_2O$). The difference between the sensed pressure and the set pressure (i.e., the medically prescribed positive pressure) generates an error value, which the system attempts to minimize by appropriately adjusting the valve step position, which appropriately adjusts the pressure delivered.

State 0 occurs when the valve step position is increased and triggers a fixed time period which leads to State 1. During this fixed time period, the difference between the instantaneous valve step position and the average valve step position is integrated over 6 time intervals. FIG. 3 shows only 3 intervals for the sake of clarity. If the summation of these 6 integrations is greater than a threshold value, then a patient inhalation is assumed and an inhalation timer is started that measures the time of inhalation.

This inhalation time measurement is terminated when a peak valve step position has been reached in State 2. The peak valve step position is determined by comparing the previous valve step position to the present valve step position and saving in memory the step position that is greater as the peak valve step position. If the peak valve step position remains unchanged for some time period (e.g., 80 ms), then the system assumes that the peak valve step position has occurred for this inhalation phase.

After State 2, the system looks for an exhalation trigger. This is accomplished by comparing two variables, both of which are based on valve step position. The equations have defined above as $VAR_1$ and $VAR_2$. If $VAR_1 \leq VAR_2$ then the trigger exists and the system moves to State 3.

In State 3, the system closes the variable position valve 108 so as to provide a lower pressure at its output. The valve 108 can be quickly and linearly closed (e.g., with a fixed slope of 3 ms/step) by reducing the valve step position to, for example, position 0 (i.e., closed) or some other position. During a significant portion of exhalation, the system now provides a lower pressure than that used during inhalation. This makes it easier for the patient to exhale.

From State 3 to State 4, the system is in open-loop control and does not vary the valve step position based on pressure or any other parameter. The valve remains in its step position during this fixed time period. As described above, the time period can be 2.5 times the previously determined inhalation time (i.e., time from State 1 to State 2). This is the pressure unloading portion of the system operation.

At State 4, the exhalation time period expires and the system gradually applies pressure to its output until the pressure once again reaches the medically prescribed positive pressure. The system is now re-loading the pressure at its output. This is accomplished by sensing the pressure at State 4, which is caused primarily by patient exhalation, and quickly changing the valve step position to meet that pressure. Hence, this phase of exhalation starts with a pressure that is dependent on the patient exhalation pressure. From State 4 to State 5, the system gradually changes the valve step position in a linear fashion (e.g., with a fixed slope of 40 ms/step) thereby gradually opening the valve until the output pressure once again reaches the higher medically prescribed positive pressure. The system is now ready for the next patient inhalation where the process repeats.

Figure 4:
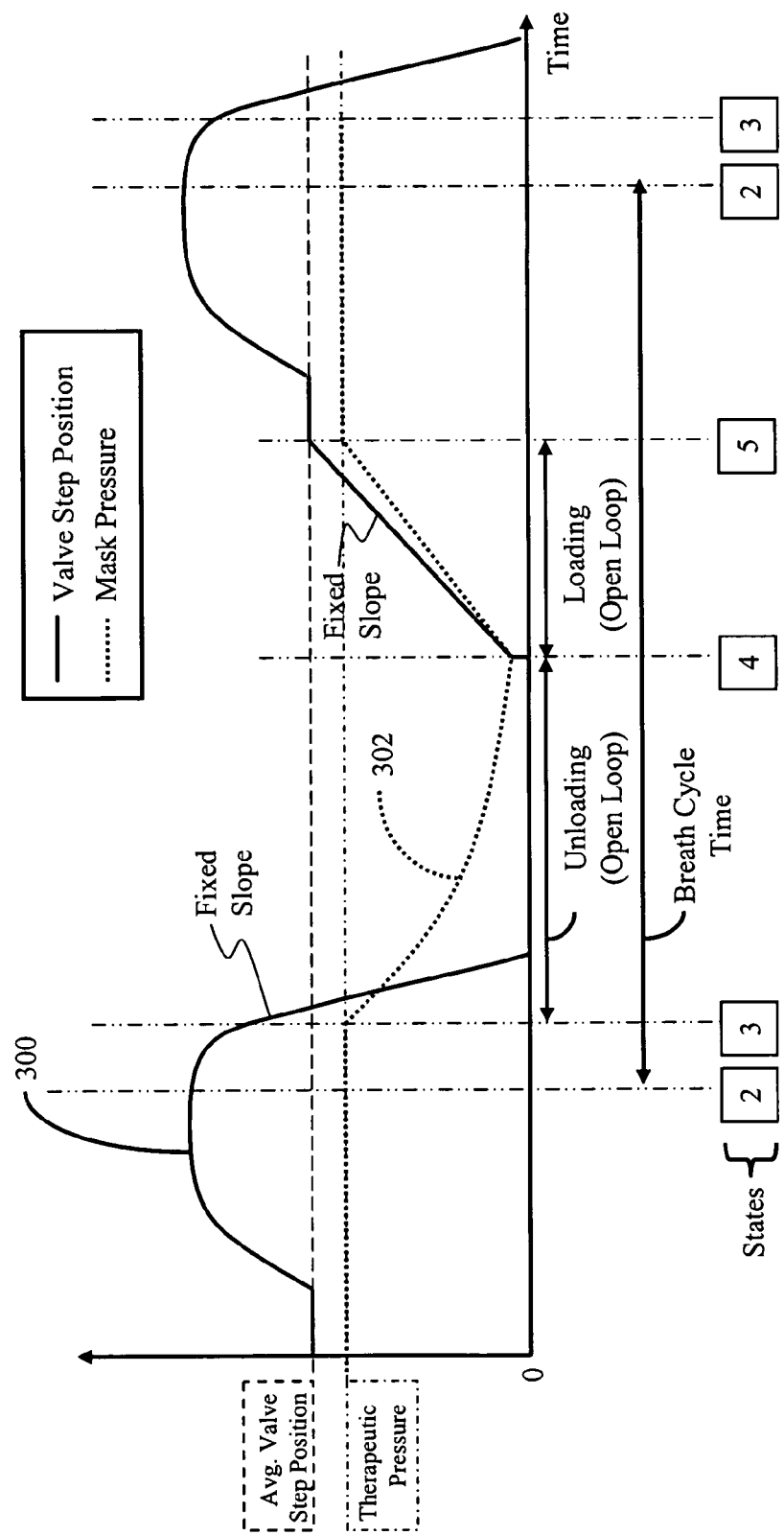
FIG. 4 is a graph illustrating a valve step position and mask pressure over time for another embodiment of the system.

FIG. 4 illustrates an embodiment of the invention directed to exhalation trigger-based control. In this regard, the control is similar to that explained above, except that no inhalation trigger is provided. In particular, a breath cycle time is measured as a function of the peak valve step position. The time between two peak valve step positions (State 2) is a measure of the breathing cycle time. The exhalation trigger at State 3, unloading portion from States 3 to 4, and loading portion from States 4 to 5 are the same as described above in connection with FIG. 3. The unloading portion (States 3 to 4) and loading portion (States 4 to 5) are defined to be percentages of the breath cycle time of the previous breath cycle(s). These percentages can range broadly, but are typically chosen so that the unloading and loading portion together are from about 50% to about 85% of the breath cycle time. The advantage of this embodiment is that it requires less processing by the controller 102.

Figure 5:
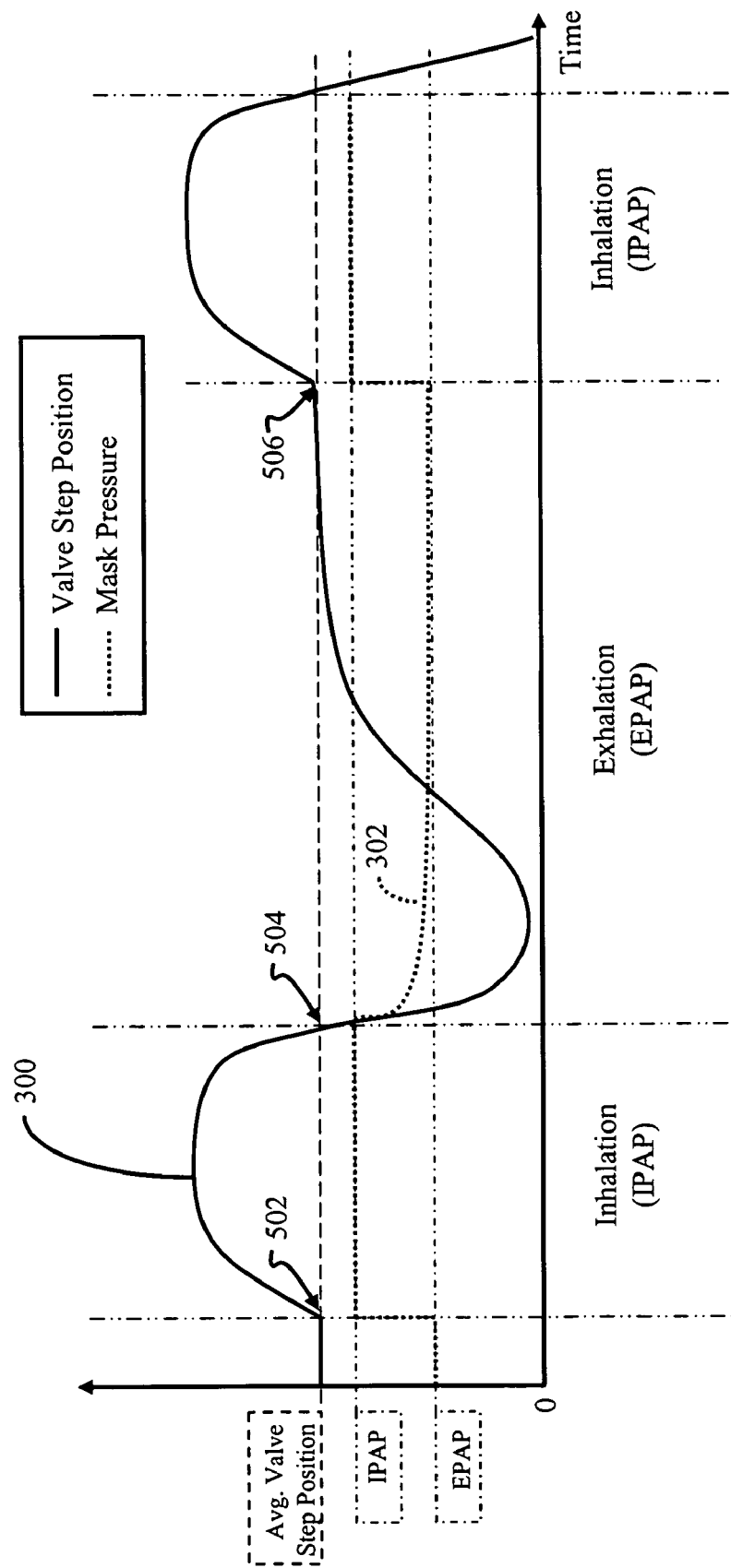
FIG. 5 is a graph illustrating a valve step position and mask pressure over time for yet another embodiment of the system.

Illustrated in FIG. 5 is an embodiment of the present invention that uses the instantaneous and average valve step position to detect the breathing state of a patient and coordinates the pressure delivered according to the detected states. In this embodiment, the system is in closed-loop control mode where it is always sensing the pressure and adjusting its output based thereon. More specifically, as the patient breathes, an average valve step position is established by virtue of the valve step position increasing to raise the pressure delivered for inhalation and decreasing to reduce the pressure delivered for exhalation based on the pressure fed back to the controller 102. By comparing the instantaneous valve step position to the average valve step position, the breathing state of the patient can be detected. If the instantaneous valve step position is above the average valve step position, the patient is inhaling. If the instantaneous valve step position is below the average valve step position, the patient is exhaling. To reduce premature or erratic triggering, the average valve step position can be offset above its true value for inhalation detection and below its true value for exhalation detection.

In FIG. 5, reference 502 indicates the instantaneous valve step position crossing the average valve step position with a positive slope. This indicates the patient is inhaling because the valve is increasing its step position to compensate for the drop in pressure caused by the patient inhalation. Reference 504 indicates the instantaneous valve step position crossing the average valve step position with a negative slope. This indicates the patient is exhaling because the valve is decreasing its step position to compensate for the increase in pressure caused by patient exhalation. According to such detection, an IPAP level can be applied during inhalation and an EPAP level can be applied during exhalation. Reference 506 indicates the next inhalation detection.

Figure 6:
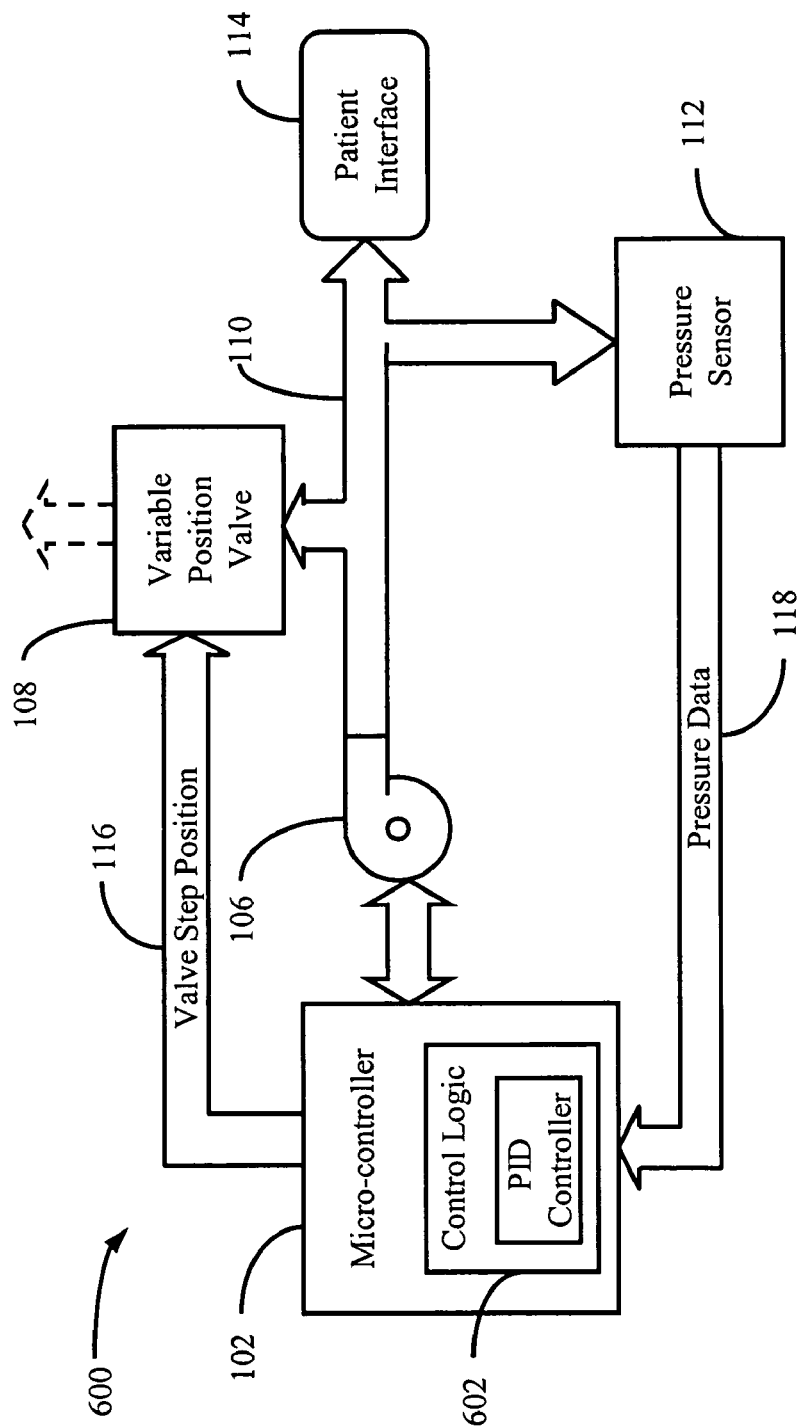
FIG. 6 is another embodiment of a system for delivering a breathing gas.

Illustrated in FIG. 6 is another embodiment of the invention in the form of system 600. System 600 is similar to system 100 (FIG. 1) except that the variable position valve 108 is in a venting position with respect to flow path 110. Also, controller 102 includes control logic 602. In this regard, breathing gas output by blower 106 travels within flow path 110 to the patient interface 114. Variable position valve 108 is positioned so that it can divert breathing gas from flow path 110 and patient interface 114. The step position of valve 108 is controlled by logic 602. While the embodiment of FIG. 6 has been described with reference to a flow/pressure control element in the form of a variable position valve 108 and a sensor element in the form of a pressure sensor 112, the flow/pressure control and sensor elements can include other types of devices. For example, the flow/pressure control element can be a variable speed blower, a variable speed blower in combination with a linear valve or solenoid valve, a variable speed blower in combination with a stepper motor controlled variable position valve, a variable speed blower in combination with a linear valve or solenoid valve and a stepper motor controlled variable position valve, or any other suitable combination of these components. The sensor element can include a flow sensor, temperature sensor, infra-red light emitter/sensor, motor current sensor, or motor speed sensor alone or in combination with the pressure sensor. The data generated from these sensor(s) is fed back to the controller 102 for processing.

Figure 7A:
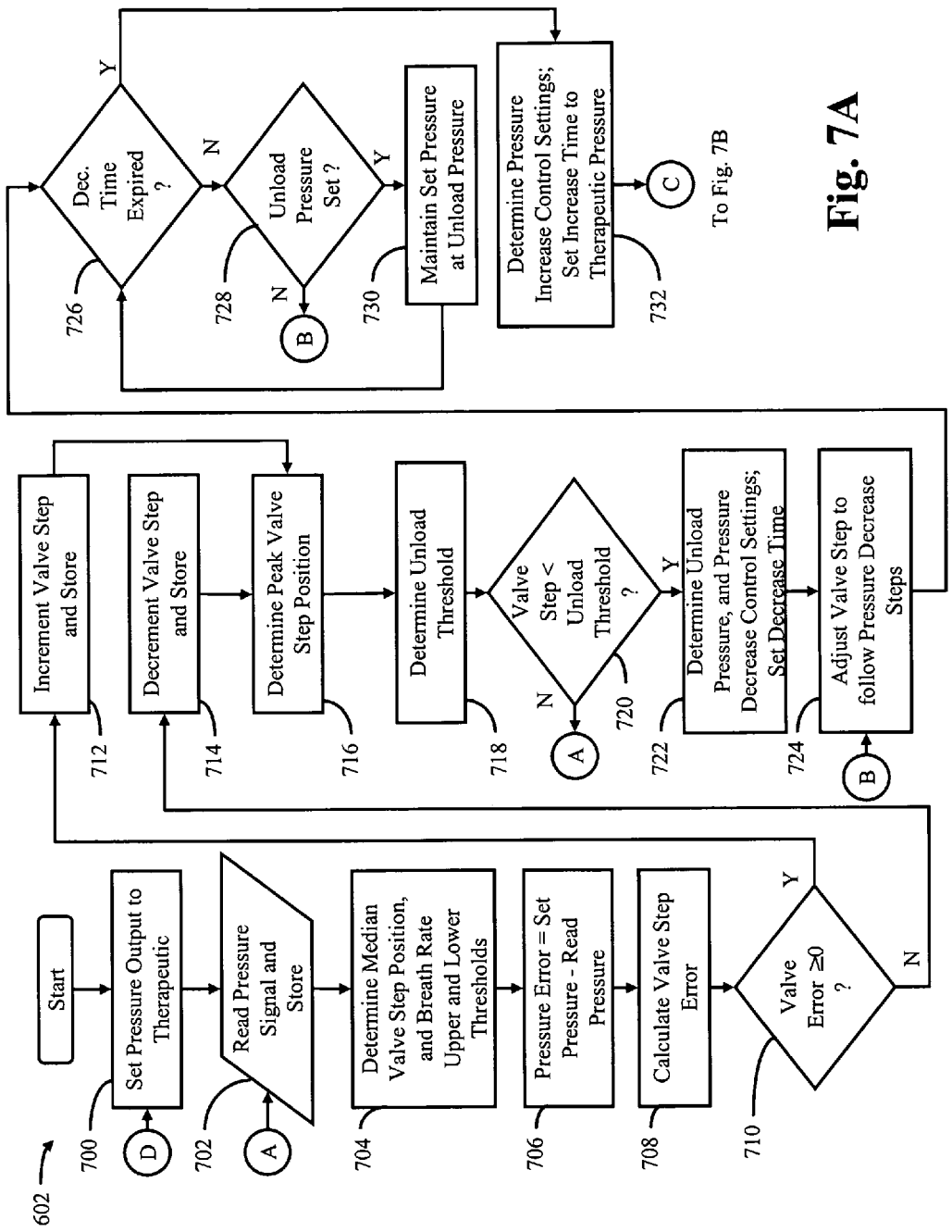
FIGS. 7A-7C illustrate another embodiment of a control process for the system.
Figure 7C:
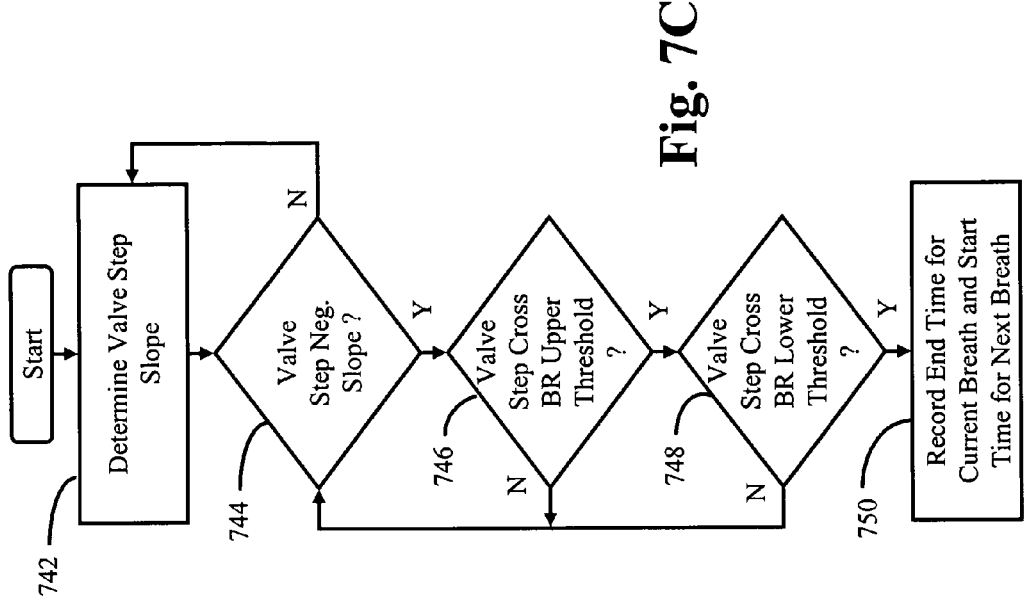
Figure 7B:
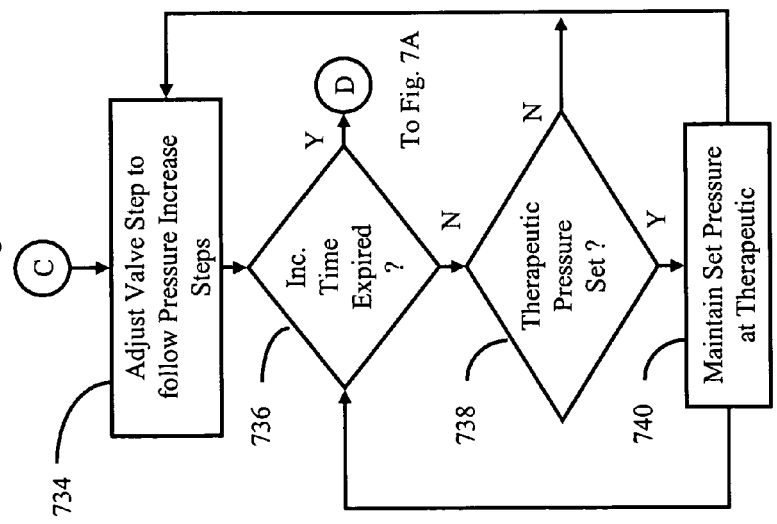

FIGS. 7A-C illustrate flowcharts directed to one embodiment of control logic 602. In block 700, the controller 102 closes the valve 108 and sets the blower 106 to a speed that produces a predetermined pressure at its output. This predetermined pressure is generally set to a medically prescribed positive pressure for a patient, plus an additional pressure component, via a pressure-to-speed look-up table that is stored in the memory of the controller 102. The additional pressure component can be a percentage of the set pressure or some other value. The additional pressure component is provided so that the medically prescribed positive pressure can be delivered under most if not all patient demand scenarios. The medically prescribed positive pressure is typically a pressure that is above the ambient pressure. For example, the prescribed pressure can range from 4 to 20 cm $H_2O$. Once the blower 106 is set to provide the required pressure, it is rarely, if ever, changed during active operation of the device. Instead, the controller 102 uses the step position of the valve 108 to modulate the output pressure.

In block 702, the pressure is read and stored. In block 704, the logic determines the median valve step position, breath rate (FIG. 7C), and upper and lower breathing rate thresholds. In one embodiment, the median valve step position and upper and lower breathing rate thresholds may be determined as follows:

Median Valve Step=(Present*0.0003)+(Previous*0.9997)

Breathing Rate Upper Threshold=Median+(Median*0.1)

Breathing Rate Lower Threshold=Median−(Median*0.1)

Wherein "Present" means present valve step position, "Previous" means previous median valve step position, and "Median" means median valve step position. The logic may initially cycle through several breathing states in determining the above values.

Once the upper and lower breathing rate thresholds are determined, the valve step position is monitored for breathing rate determination. Referring to FIG. 7C, the slope of the valve step change is determined in block 742. This may be accomplished by comparing the present and one or more previous valve step positions over time. If the slope of the valve step position is negative in block 744, the logic advances to block 746. Otherwise, the logic loops back to blocks 742 or 704 to continue processing until the next valve step change. In block 746, the logic tests to determine if the valve step position has fallen below the upper breathing rate (BR) threshold (see FIG. 8B). If so, the logic advances to block 748 where it tests to determine if the valve step position has fallen below the lower breathing rate (BR) threshold (see FIG. 8B). If so, the logic advances to block 750 where the end time is recorded for the current breath and the start time is recorded for the next breath. Based on the start and end time of each breath, a breath rate (e.g., breaths/minute) can be calculated and stored for subsequent use.

Referring back to FIG. 7A, a pressure error is generated by comparing the set pressure to the pressure read by the pressure sensor 112 in block 706. In block 708, the pressure error is used to generate a valve step error, which can be according to the following:

$$V_{error}=(P_{error}*P)+(D_{error}*D)+(S_{error}*S)$$

Where "$V_{error}$" is the valve step error, "$P_{error}$" is the pressure error, "$D_{error}$" is the pressure error difference between the present and the previous pressure error calculation, "$S_{error}$" is the summation of the pressure errors, and "P," "D," and "S" are constants. The "$V_{error}$" equation generally defines a Proportional Integral Derivative (hereinafter PID) servo controller. Generally, the constants of "P," "D," and "S" are selected after empirical study of the behavior of the system. Additionally, theoretical values can also be selected for the constants. This PID servo control is active substantially throughout the logic's operation, though intermittent operation may also be acceptable during portions of the patient's breathing states. As will be described, the logic utilizes various pressure settings for the PID controller to generate the proper pressure outputs given the effects of the patient's breathing characteristics on the system's performance.

Block 710 tests to determine whether the valve step error is greater than or equal to zero. If so, the logic advances to block 712 where the valve step position is incremented one or more steps so as to try to reduce the error. Otherwise, the logic advances to block 714 where the valve step position is decremented one or more steps to try and reduce the error. It should be noted that the valve step position employed by the logic may or may not equal one step of the stepper motor that controls the movement of the valve. For example, one valve step may be equal to a half step movement of the valve's stepper motor.

After either steps 712 or 714, the logic advances to block 716 where the valve step is monitored for a peak valve step position. In one embodiment, the logic determines the inhalation threshold according to the following:

Inhalation Threshold=[(Peak−Median)*0.5]+Median

Wherein "Peak" is the peak valve step position from one or more previous breath cycles, "Median" is the median valve step position, and 0.5 is an exemplary scaling factor. Other scaling factor values may be used in other embodiments. After the present valve step position exceeds the inhalation threshold, the logic begins determining the peak valve step position. The peak valve step position is determined by comparing the present valve step position to the previous valve step position and choosing the greater value.

In block 718, the logic determines the unload threshold according to the following:

Unload Threshold=[(Peak−Median)*T]+Median

Wherein "Peak" is the peak valve step position from one or more previous breath cycles, "Median" is the median valve step position, and "T" is a percent unloading trigger value that is determined from a look-up table based on the determined breaths per minute. One example of a breaths per minute based look-up table is shown below in Table 1:

TABLE 1

| Breaths per minute | T (% unloading) |
| --- | --- |
| 0 | −0.15 |
| 1 | −0.15 |
| 2 | −0.15 |
| 3 | −0.15 |
| 4 | −0.15 |
| 5 | −0.15 |
| 6 | −0.15 |
| 7 | −0.10 |
| 8 | −0.10 |
| 9 | −0.10 |
| 10 | 0.00 |
| 11 | 0.00 |
| 12 | 0.10 |
| 13 | 0.10 |
| 14 | 0.12 |
| 15 | 0.15 |
| 16 | 0.17 |
| 17 | 0.20 |
| 18 | 0.23 |
| 19 | 0.25 |
| 20 | 0.26 |
| 21 | 0.28 |
| 22 | 0.30 |
| 23 | 0.32 |
| 24 | 0.34 |
| 25 | 0.37 |
| 26 | 0.37 |
| 27 | 0.37 |
| 28 | 0.37 |
| 29 | 0.37 |
| 30 | 0.37 |

In Table 1, each "Breaths per minute" value has a corresponding "T (% unloading)" value associated therewith in the form of values "X," "Y," and "Z", which are typically equal to or less than 1. The "T (% unloading)" values can be the same or different for any given "Breaths per minute" value and determine how soon the unloading cycle starts with respect to the median valve step position. For example, a "T (% unloading)" value closer to 1 would raise the unload threshold to be higher away from the median valve step position, thus causing the triggering of a pressure reduction sooner with respect to valve step position. A "T (% unloading)" valve step closer to zero (0) would lower the unload threshold bringing it closer to the median valve step position, thus causing the triggering of a pressure reduction later with respect to the valve step position. Generally, the larger the "Breaths per minute" valve, the larger the "T (% unloading)" value. It should also be noted that one or more "Breaths per minute" values may have the same or different "T (% unloading)" values associated therewith.

In block 720, the logic tests to determine whether the valve step position has fallen below the unload threshold. If not, the logic loops back to block 702 to continue the active PID servo control of the valve step position. If so, the logic advances to block 722. In block 722, the logic determines the unload pressure and the pressure decrease control waveform and associated pressure settings. Also, a decrease timer is set. In one embodiment, the unload pressure is determined as follows:

Unload Pressure=$P_{set}-[P_{set}*((\Delta V*V_{scale})/K)*S]$ where "$P_{set}$" is the medically described positive pressure, "$\Delta V$" is the change in valve step position defined by (Peak−Median), "$V_{scale}$" is a value selected from Table 2 (below) and is based on $P_{set}$, "K" is a constant (e.g., in the range of 2000-4000, such as 3000) and "S" is a constant in the range of 1-3 but can be smaller than 1 and larger than 3. If the logic desires to simply maintain the pressure due to certain operating conditions, the "S" constant may be set to 0 so that the unload pressure is equal to the prescribed pressure. The value of "$V_{scale}$" may be described pressure ($P_{set}$), for example, as shown in Table 2.

TABLE 2

| $P_{set}$ | $V_{scale}$ |
|---|---|
| 0 | 0 |
| 1 | 0 |
| 2 | 0 |
| 3 | 0 |
| 4 | 0.28 |
| 5 | 0.28 |
| 6 | 0.25 |
| 7 | 0.25 |
| 8 | 0.25 |
| 9 | 0.23 |
| 10 | 0.23 |
| 11 | 0.22 |
| 12 | 0.22 |
| 13 | 0.18 |
| 14 | 0.15 |
| 15 | 0.15 |
| 16 | 0.14 |
| 17 | 0.14 |
| 18 | 0.12 |
| 19 | 0.12 |
| 20 | 0.12 |

In Table 2, the $P_{set}$ values range from 0 to 20 and represent a range of medically prescribed positive pressure values. Each $P_{set}$ value has a corresponding $V_{scale}$ value ("A," "B," "C," etc.) associated with it that can be determined either by prior empirical or theoretical modeling of the system. For example, if system 600 is configured to work with a wide range of patient interfaces 114, each type of patient interface 114 may cause slight differences in the performance of system 600 at a give pressure of $P_{set}$. Hence, one may choose to determine the $V_{scale}$ values after understanding the impact of various patient interfaces on the system performance. Generally, the "$V_{scale}$" values may range from 0 to 0.28 as shown in Table 2, but other embodiments may go beyond this range. Moreover, certain safeguards may be employed to not allow the unload pressure to fall beyond certain levels. For example, if the pressure $P_{set}$ is 4 cm $H_2O$, then the logic may not allow any pressure unloading due to the set pressure already being a very low medically prescribed positive pressure. However, in most circumstances, the Unload Pressure determination results in a value that is less than the medically prescribed positive pressure.

Further, in block 722, the logic determines, for example, 195 pressure settings that define the control waveform for the pressure setting reduction down to the unload pressure setting. These pressure settings are used by the active PID servo control. In one embodiment, the 195 pressure settings are governed by a pressure decrease timer (e.g., 780 ms). In one embodiment, the control waveform for the unload period can be defined by a ramp down portion and a hold portion. The ramp down portion may include 10 pressure settings that sequentially reduce the pressure setting from the therapeutic pressure setting to the unload pressure setting in, for example, 40 ms comprised of, for example, ten 4 ms increments. The hold portion maintains the pressure setting at the unload pressure setting over, for example, 740 ms comprised of, for example, 185 four ms periods. It should be noted that other values may be chosen and the described values are merely meant to illustrate one embodiment of the invention. It should also be noted that the sensed pressure can be used to re-determine or adjust the control waveform during the ramping and/or hold portions of the unload period.

In block 724, the valve step position is adjusted in an attempt to have the sensed pressure follow the pressure settings of the determined control waveform for the pressure setting reduction down to the unload pressure setting. In other words, block 724 uses the same logic as blocks 706-714 because the active PID servo control is used to correct the valve step position as the pressure settings of the control waveform are used for the desired pressure setting. For example, each of the pressure settings defines a "Set Pressure" that is compared to the sensed pressure to generate a pressure error that is used by the active PID servo control.

In block 726, the logic tests to determine whether the pressure decrease timer (e.g., 780 ms) has expired. If so, the logic advances to block 732. If not, the logic advances to block 728 where it determines whether the unload pressure setting in the control waveform has been reached. If the pressure decrease timer has expired, the logic advances to block 732 where it prepares for pressure reloading back up to the medically prescribed positive pressure. If the unload pressure setting has not been reached in block 728, the logic loops back to block 724 and continues the active PID servo control of the valve step position according to the pressure settings of the control waveform. If the unload pressure setting has been reached in block 728, the logic advances to block 730 where the unload pressure setting is maintained through the active PID servo control of the valve step position until the pressure decrease timer expires.

After the pressure decrease timer has expired, the logic executes block 732 where it determines the pressure increase control waveform and associated pressure settings. Also, a pressure increase timer is set. In one embodiment, the logic determines, for example, 100 pressure settings that define the control waveform for the pressure increase up to the medically prescribed positive pressure (therapeutic pressure). This waveform is based on the pressure setting at the expiration of the decrease timer and the medically prescribed positive pressure. In one embodiment, the pressure increase timer may be set to 400 ms. In one embodiment, the control waveform for the load period can be defined by a ramp up portion. The ramp up portion may include 100 pressure settings that sequentially increase the pressure setting from the unload pressure setting to the therapeutic pressure setting in, for example, 400 ms comprised of, for example, one hundred 4 ms increments. In another embodiment, control waveform for the load period can be defined by a ramp up portion and a hold portion in similar fashion to the control waveform for the unload period described above. Once again, it should be noted that other values may be chosen and the described values are merely meant to illustrate one embodiment of the invention. It should also be noted that the sensed pressure can be used to re-determine or adjust the control waveform during the ramping and/or hold portions of the load period.

In block 734, the valve step position is adjusted in an attempt to have the sensed pressure follow the pressure settings of the determined control waveform for the pressure setting increase up to the medically prescribed positive pressure setting. In other words, block 734 uses the same logic as blocks 706-714 and 724 because the active PID servo control is used to correct the valve step position as the pressure settings of the control waveform are used for the desired pressure setting.

In block 736, the logic tests to determine whether the pressure increase timer (e.g., 400 ms) has expired. If so, the logic advances to block 700 wherein the pressure is set to the medically prescribed positive pressure. If not, the logic advances to block 738 where it determines whether the medically prescribed positive airway pressure setting (e.g., therapeutic pressure setting) in the control waveform has been reached. If the medically prescribed positive pressure setting has not been reached in block 738, the logic loops back to block 734 and continues the active PID servo control of the valve step position according to the pressure settings of the control waveform. If the therapeutic pressure has been reached in block 738, the logic advances to block 740 where the medically prescribed positive pressure setting is maintained through the active PID servo control of the valve step position until the pressure increase timer expires. Once the pressure increase timer expires, the logic loops back to block 700 and the process repeats for the next breathing cycle.

Referring now to FIGS. 8A-8C, the lung flow, valve step position, control pressure and sensed pressure over time for the embodiment illustrated in FIG. 6 are shown. FIG. 8A illustrates the flow of breathing gas into and out of the lung over time. FIG. 8B illustrates the valve step position over time, along with the median valve step, upper and lower breathing rate (BR) thresholds, inhalation threshold, and unload threshold. The use of these values and thresholds have been described with reference to the logic of FIGS. 7A-7C. FIG. 8C illustrates the control pressure waveform that determines the pressure settings and the sensed pressure by the system. During inhalation, the PID servo controller tries to maintain the set pressure, which is the medically prescribed positive pressure for the patient. This causes the valve step position to change due to patient demand, which increases to a peak valve step position and then decreases. During this phase, the peak valve step position is monitored and the median valve step position is calculated. When the valve step position falls below the unload threshold, the unload pressure is determined along with the pressure decrease control waveform and associated pressure settings that are used by the active PID servo control to reduce the pressure down to the unload pressure. A pressure decrease timer is also started. If the sensed pressure reaches the unload pressure prior to expiration of the decrease timer due to the patient's breathing characteristics, the unload pressure is maintained by the active PID servo controller until the decrease timer expires. Once the decrease timer expires, independent of whether the unload pressure has been reached, a pressure increase control waveform and associated pressure settings are determined based on the sensed pressure at the expiration of the decrease timer and the medically prescribed positive pressure. The pressure increase control waveform is used by the active PID servo controller to raise the pressure back up to the set therapeutic pressure during the increase time period. Because of the active PID servo controller and the effect of the patient's breathing characteristics, the pressure may rise to the required therapeutic level prior to expiration of the increase timer.

Figure 9:
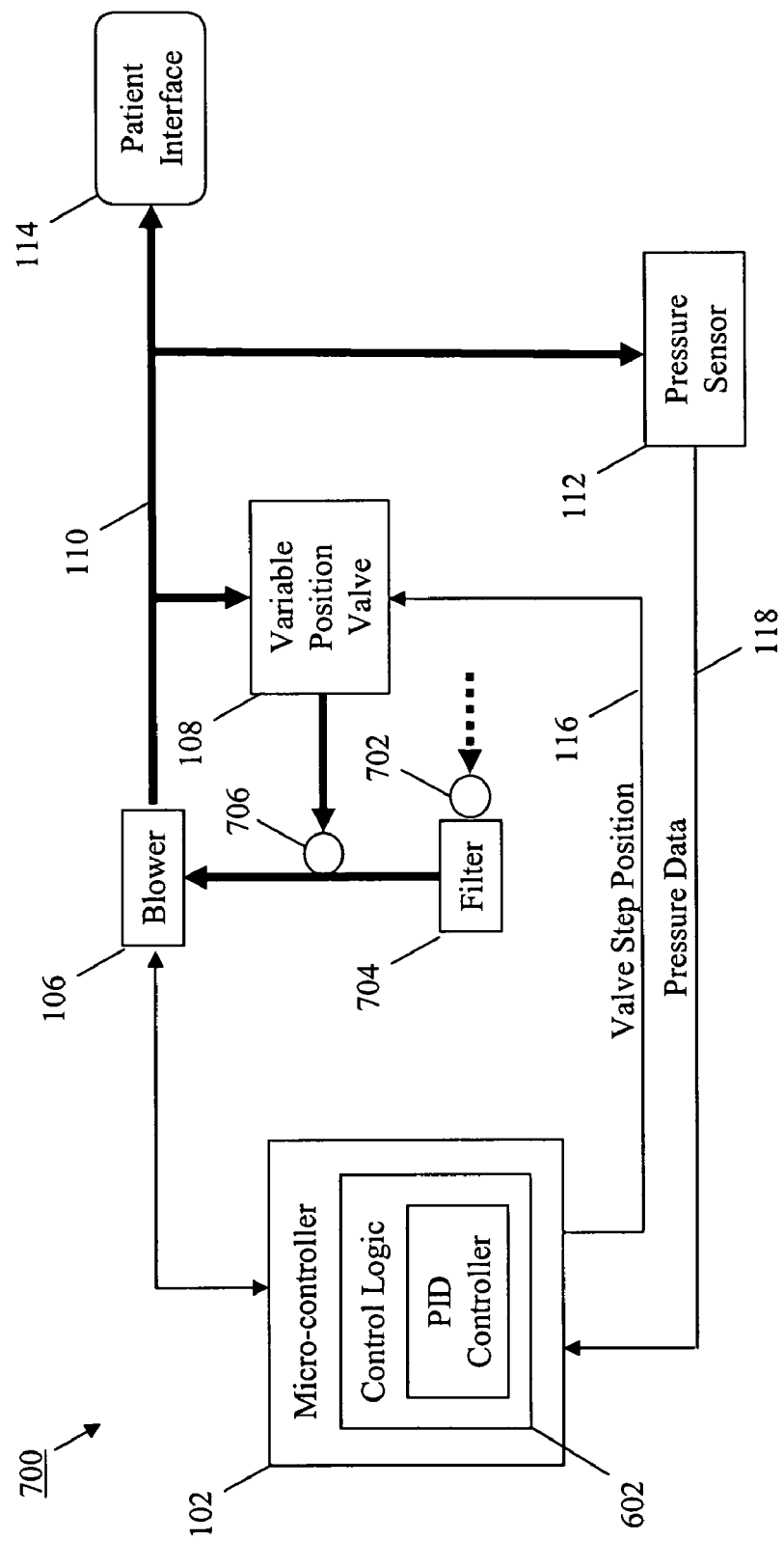
FIG. 9 is yet another embodiment of a system for delivering a breathing gas.

Illustrated in FIG. 9 is yet another embodiment of the invention in the form of system 700. System 700 is similar to system 600 (FIG. 6). FIG. 9 depicts an ambient input 702 and a filter 704 that provide ambient air to an input associated with the blower 106. The ambient input 702 and filter 704 are implied in the previously described systems of FIGS. 1 and 6 and corresponding blower operations. System 700 also includes a non-ambient input 704 which receives breathing gas diverted from the flow path 110 by the variable position valve 108. This arrangement is different than in FIG. 6, where the variable position valve 108 diverts breathing gas, but does not necessarily direct the diverted breathing gas back to the blower 106. Otherwise, the system 700 operates in the same manner as system 600 which is described above in references to FIGS. 6, 7A-C, and 8A-C. Moreover, options, variations, and alternatives described above in regard to system 600 are equally suitable for system 700, except where they conflict with diverting the breathing gas to the non-ambient input 704. In other embodiment, one or more additional filters between the filter 704 and the blower 106 may be provided.

While the present invention has been illustrated by the description of embodiments thereof, and while the embodiments have been described in considerable detail, it is not the intention of this specification to restrict or in any way limit the scope of the appended claims to such detail. Additional advantages and modifications will readily appear to those skilled in the art. For example, valve step position can be changed according to non-linear function as an alternate, addition or in combination with linear functions. Alternate or additional parameters of the flow gas can be sensed including flow rates through the use of flow sensors to modulate valve step position. More specifically, the direction of flow and/or the change in flow rates (e.g., instantaneous and average) can also be used. Therefore, the invention, in its broader aspects, is not limited to the specific details, the representative apparatus, and illustrative examples shown and described. Accordingly, departures may be made from such details without departing from the spirit or scope of the applicant's general inventive concept.

What is claimed is:

1. A method of providing a breathing gas comprising:
   a) sensing a sensed parameter associated with delivery of the breathing gas;
   b) changing a control parameter associated with a flow/pressure control element in response to a difference between the sensed parameter and a first predetermined sensed parameter value during an inhalation state of a breathing cycle;
   c) determining a transition from the inhalation state to an exhalation state of the breathing cycle based at least in part on the changing control parameter;
   d) changing the control parameter to cause a first change in the sensed parameter during an unload portion of the exhalation state based at least in part on the determined transition; and
   e) changing the control parameter to cause a second change in the sensed parameter during a load portion of the exhalation state based at least in part on the first predetermined sensed parameter value.

2. The method of claim 1 wherein the sensed parameter is breathing gas pressure, breathing gas flow, breathing gas temperature, or breathing gas composition.

3. The method of claim 1 wherein the flow/pressure control element includes a variable position valve and the control parameter includes a valve step position.

4. The method of claim 1 wherein the flow/pressure control element includes a variable speed blower and the control parameter includes a blower speed.

5. The method of claim 1 wherein the determining in c) comprises determining an average valve step position.

6. The method of claim 1 wherein the determining in c) comprises identifying an instantaneous valve step position.

7. The method of claim 1 wherein the determining in c) comprises determining a peak valve step position.

8. The method of claim 7 wherein determining the peak valve step position comprises identifying a highest valve step position between a present valve step position and one or more previous valve step positions and if the highest valve step position does not change for a predetermined peak valve step time, identifying the highest valve step position as the peak valve step position.

9. The method of claim 1 wherein the determining in c) is based at least in part on a predetermined percentage threshold value.

10. The method of claim 1 wherein the changing in d) comprises determining an inhale time associated with the inhalation state.

11. The method of claim 10 wherein the changing in d) comprises determining an exhale time associated with the unload portion of the exhalation state and based at least in part on the determined inhale time.

12. The method of claim 11 wherein the duration of the unload portion of the exhalation state is based at least in part on the exhale time.

13. The method of claim 11 wherein the exhale time is based at least in part on a predetermined exhale time factor.

14. The method of claim 1 wherein the changing in d) is based at least in part on an unloading function.

15. The method of claim 1 wherein the changing in d) is based at least in part on a second predetermined sensed parameter value.

16. The method of claim 1 wherein the changing in d) comprises determining a peak valve step position.

17. The method of claim 1 wherein the changing in e) is based at least in part on a loading function.

18. A method of providing a breathing gas comprising:
a) sensing a breathing gas pressure associated with delivery of the breathing gas;
b) detecting a start of an inhalation state of a breathing cycle;
c) changing a valve step position associated with a variable position valve in response to a difference between the sensed breathing gas pressure and a first predetermined breathing gas pressure value during the inhalation state;
d) determining a transition from the inhalation state to an exhalation state of the breathing cycle based at least in part on the changing valve step position;
e) changing the valve step position to cause a first change in the breathing gas pressure during an unload portion of the exhalation state based at least in part on the determined transition; and
f) changing the valve step position to cause a second change in the breathing gas pressure during a load portion of the exhalation state based at least in part on the first predetermined breathing gas pressure value.

19. The method of claim 18 wherein the detecting in b) comprises:
g) determining an average valve step position;
h) integrating a difference between an instantaneous valve step position and the average valve step position over a predetermined integration time to produce a summation; and
i) identifying the start of the inhalation state after the summation is greater than a predetermined start of inhalation threshold value.

20. The method of claim 18 wherein the determining in d) comprises:
g) calculating a first transition variable based at least in part on an instantaneous valve step position;
h) calculating a second transition variable based at least in part on a peak valve step position; and
i) identifying the transition from the inhalation state to the exhalation state after the first transition variable is less than or equal to the second transition variable.

21. The method of claim 20 wherein the calculating in g) comprises:
j) determining an average valve step position;
k) identifying the instantaneous valve step position; and
l) calculating the first transition variable by subtracting the average valve step position from the instantaneous valve step position.

22. The method of claim 20 wherein the calculating in h) comprises:
j) determining an average valve step position;
k) determining a peak valve step position for the inhalation state; and
l) calculating the second transition variable by multiplying a difference between the peak valve step position and the average valve step position by a predetermined percentage threshold value.

23. The method of claim 18 wherein the changing in e) comprises:
g) determining an inhale time associated with the inhalation state;
h) determining an exhale time associated with the unload portion of the exhalation state and based at least in part on the determined inhale time;
i) beginning the exhale time after the transition from the inhalation state to the exhalation state;
j) decrementing the valve step position according to an unloading function until a second predetermined breathing gas pressure value is achieved; and
k) changing the valve step position in response to a difference between the sensed breathing gas pressure and the second predetermined breathing gas pressure value after the second predetermined breathing gas pressure value is achieved and until the exhale time expires.

24. The method of claim 23 wherein the determining in g) comprises:
l) starting an inhalation timer after the start of the inhalation state is detected;
m) determining a peak valve step position for the inhalation state; and
n) stopping the inhalation timer after the peak valve step position for the inhalation state is determined.

25. The method of claim 23 wherein the exhale time in h) is a product of a predetermined exhale time factor and the determined inhale time.

26. The method of claim 18 wherein the changing in f) comprises:
g) incrementing the valve step position according to a loading function until the first predetermined breathing gas pressure value is achieved; and
h) changing the valve step position in response to a difference between the sensed breathing gas pressure and the first predetermined breathing gas pressure value after the first predetermined breathing gas pressure value is achieved.

27. A method of providing a breathing gas comprising:
a) sensing a breathing gas pressure associated with delivery of the breathing gas;
b) determining a breath cycle time associated with at least a portion of a current inhalation state of a current breathing cycle and a portion of a previous breathing cycle;
c) changing a valve step position associated with a variable position valve in response to a difference between the sensed breathing gas pressure and a first predetermined breathing gas pressure value during the current inhalation state;

d) determining a transition from the current inhalation state to a current exhalation state of the current breathing cycle based at least in part on the changing valve step position;

e) changing the valve step position to cause a first change in the breathing gas pressure during an unload portion of the current exhalation state based at least in part on the determined transition; and f) changing the valve step position to cause a second change in the breathing gas pressure during a load portion of the current exhalation state based at least in part on the first predetermined breathing gas pressure value.

28. The method of claim 27 wherein the determining in b) comprises:

g) determining a peak valve step position for a previous inhalation state of the previous breathing cycle;

h) starting a breath cycle timer after the peak valve step position for the previous breathing cycle is determined;

i) determining a peak valve step position for the current inhalation state; and j) stopping the breath cycle timer after the peak valve step position for the current inhalation state is determined.

29. The method of claim 27 wherein the determining in d) comprises:

g) calculating a first transition variable based at least in part on an instantaneous valve step position;

h) calculating a second transition variable based at least in part on a peak valve step position; and i) identifying the transition from the current inhalation state to the current exhalation state after the first transition variable is less than or equal to the second transition variable.

30. The method of claim 29 wherein the calculating in g) comprises:

j) determining an average valve step position;

k) identifying the instantaneous valve step position; and l) calculating the first transition variable by subtracting the average valve step position from the instantaneous valve step position.

31. The method of claim 29 wherein the calculating in h) comprises:

j) determining an average valve step position;

k) determining a peak valve step position for the current inhalation state; and l) calculating the second transition variable by multiplying a difference between the peak valve step position and the average valve step position by a predetermined percentage threshold value.

32. The method of claim 27 wherein the changing in e) comprises:

g) determining an unloading time associated with the unload portion of the current exhalation state and based at least in part on the determined breath cycle time;

h) beginning the unloading time after the transition from the current inhalation state to the current exhalation state;

i) decrementing the valve step position according to an unloading function until a second predetermined breathing gas pressure value is achieved; and j) changing the valve step position in response to a difference between the sensed breathing gas pressure and the second predetermined breathing gas pressure value after the second predetermined breathing gas pressure value is achieved and until the unloading time expires.

33. The method of claim 32 wherein the unloading time in g) is a product of a predetermined unload time factor and the determined breath cycle time.

34. The method of claim 27 wherein the changing in f) comprises:

g) determining a loading time associated with the load portion of the current exhalation state and based at least in part on the determined breath cycle time;

h) beginning the loading time after the unload portion of the current exhalation state;

i) incrementing the valve step position according to a loading function until the first predetermined breathing gas pressure value is achieved; and j) changing the valve step position in response to a difference between the sensed breathing gas pressure and the first predetermined breathing gas pressure value after the first predetermined breathing gas pressure value is achieved and until the loading time expires.

35. The method of claim 34 wherein the loading time in g) is a product of a predetermined load time factor and the determined breath cycle time.

36. A method of providing a breathing gas comprising:

a) sensing a sensed parameter associated with delivery of the breathing gas;

b) changing a control parameter associated with a flow/pressure control element in response to a difference between the sensed parameter and a first predetermined sensed parameter value during a first portion of a current breathing cycle;

c) determining a transition from the first portion to a second portion of the current breathing cycle based at least in part on the changing control parameter;

d) changing the control parameter to cause a first change in the sensed parameter during the second portion of the current breathing cycle based at least in part on the determined transition; and e) changing the control parameter to cause a second change in the sensed parameter during a third portion of the current breathing cycle based at least in part on the first predetermined sensed parameter value.

37. The method of claim 36 wherein the sensed parameter is breathing gas pressure, breathing gas flow, breathing gas temperature, or breathing gas composition.

38. The method of claim 36 wherein the flow/pressure control element includes a variable position valve and the control parameter includes a valve step position.

39. The method of claim 36 wherein the flow/pressure control element includes a variable speed blower and the control parameter includes a blower speed.

40. The method of claim 36 wherein the changing in b) comprises:

f) determining a valve step error based at least in part on the sensed parameter and the first predetermined sensed parameter value; and g) changing the control parameter to minimize the valve step error.

41. The method of claim 40 wherein the sensed parameter is a breathing gas pressure and the determining in f) comprises:

f) determining a current pressure error by comparing the first predetermined sensed parameter value to the sensed parameter;

g) determining a pressure error difference between the current pressure error and a previous pressure error;

h) determining a pressure error sum by adding the current pressure error and the previous pressure error; and i) calculating the valve step error by adding a first product of the current pressure error and a first constant, a second product of the pressure error difference and a second constant, and a third product of the pressure error sum and a third constant.

42. The method of claim 36 wherein the flow/pressure control element is a variable position valve, the control parameter is a valve step position, and the determining in c) comprises:
   f) determining the unload threshold value; and
   g) determining whether the changing valve step position is less than the unload threshold value.

43. The method of claim 42 wherein the determining in f) comprises:
   h) determining a breath rate;
   i) determining a median valve step position;
   j) determining a peak valve step position for one or more previous breath cycles;
   k) identifying a predetermined percentage unloading factor associated with the determined breath rate; and
   l) calculating the unload threshold value based at least in part on the determined median valve step position.

44. The method of claim 43 wherein the determining in h) comprises:
   m) recording a start time for a current breath during a previous breathing cycle;
   n) recording an end time for the current breath during a current breathing cycle; and
   o) calculating the breath rate based on the start and end times for the current breath.

45. The method of claim 44 wherein the recording in m) comprises:
   p) determining an upper breath rate threshold value;
   q) determining a lower breath rate threshold value;
   r) identifying when a previous slope of a previous valve step position change is negative during the previous breathing cycle;
   s) monitoring the valve step position as it becomes less than the upper breath rate threshold value during the previous breathing cycle; and
   t) recording the start time for the current breath after the valve step position becomes less than the lower breath rate threshold value.

46. The method of claim 45 wherein the determining in p) comprises:
   u) calculating the upper breath rate threshold value by adding a predetermined percentage of the median valve step position to the median valve step position.

47. The method of claim 45 wherein the determining in q) comprises:
   u) calculating the lower breath rate threshold value by subtracting a predetermined percentage of the median valve step position from the median valve step position.

48. The method of claim 44 wherein the recording in n) comprises:
   p) determining an upper breath rate threshold value;
   q) determining a lower breath rate threshold value;
   r) identifying when a current slope of a current valve step position change is negative during the current breathing cycle;
   s) monitoring the valve step position as it becomes less than the upper breath rate threshold value during the current breathing cycle; and
   t) recording an end time for the current breath after the valve step position becomes less than the lower breath rate threshold value during the current breathing cycle.

49. The method of claim 43 wherein the determining in i) comprises:
   m) identifying a present valve step position; and
   n) calculating the median valve step position by adding a first predetermined percentage of the present valve step position to a second predetermined percentage of a previous median valve step position, wherein a sum of the first and second predetermined percentages is one.

50. The method of claim 43 wherein the determining in j) comprises:
   m) determining an inhalation threshold;
   n) after the changing valve step position exceeds the inhalation threshold, identifying a highest valve step position between a present valve step position and one or more previous valve step positions; and
   o) if the highest valve step position does not change for a predetermined peak valve step time, identifying the highest valve step position as the peak valve step position.

51. The method of claim 50 wherein the determining in m) comprises:
   p) determining a difference between the peak valve step position and the median valve step position;
   q) determining a product of the determined difference and a predetermined inhalation scaling factor; and
   r) adding the determined product to the median valve step position.

52. The method of claim 43 wherein the calculating in l) comprises:
   m) determining a difference between the peak valve step position and the median valve step position;
   n) determining a product of the determined difference and the predetermined percentage unloading factor; and
   o) adding the determined product to the median valve step position.

53. The method of claim 36 wherein the changing in d) comprises:
   f) determining a second predetermined sensed parameter value;
   g) setting a decrease timer to a predetermined unload time;
   h) determining a sequence of predetermined sensed parameter values for the second portion of the current breathing cycle based at least in part on the first and second predetermined sensed parameter values; and
   i) changing the control parameter based at least in part on the sequence of predetermined sensed parameter values until the decrease timer is expired.

54. The method of claim 51 wherein the flow/pressure control element is a variable position valve, the control parameter is a valve step position, the first predetermined sensed parameter value is a prescribed pressure, the second predetermined sensed parameter value is an unload pressure, and the determining in f) comprises:
   j) determining a peak valve step position;
   k) determining a median valve step position;
   l) calculating a pressure offset by subtracting the median valve step position from the peak valve step position to obtain a first intermediate result, multiplying the first intermediate result by a first constant to obtain a second intermediate result, and multiplying the second intermediate result by the prescribed pressure; and
   m) calculating the unload pressure by subtracting the pressure offset from the prescribed pressure.

55. The method of claim 36 wherein the changing in e) comprises:
   f) determining a second predetermined sensed parameter value;

g) setting an increase timer to a predetermined load time;

h) determining a sequence of predetermined sensed parameter values for the third portion of the current breathing cycle based at least in part on the first and second predetermined sensed parameter values; and i) changing the control parameter based at least in part on the sequence of predetermined sensed parameter values until the increase timer is expired.

56. A method of providing a breathing gas comprising:

a) sensing a breathing gas pressure associated with delivery of the breathing gas;

b) changing a valve step position associated with a variable position valve in response to a difference between the sensed breathing gas pressure and a first predetermined breathing gas pressure value during a first portion of a current breathing cycle;

c) determining a transition from the first portion to a second portion of the current breathing cycle based at least in part on the changing valve step position;

d) changing the valve step position to cause a first change in the breathing gas pressure during the second portion of the current breathing cycle based at least in part on the determined transition; and e) changing the valve step position to cause a second change in the breathing gas pressure during a third portion of the current breathing cycle based at least in part on the first predetermined breathing gas pressure value.

57. The method of claim 56 wherein the changing in b) comprises:

f) determining a valve step error based at least in part on the sensed parameter and the first predetermined sensed parameter value; and g) changing the control parameter to minimize the valve step error.

58. The method of claim 56 wherein determining in c) comprises:

f) determining the unload threshold value; and g) determining whether the changing valve step position is less than the unload threshold value.

59. The method of claim 56 wherein the changing in d) comprises:

f) determining a second predetermined breathing gas pressure value;

g) setting a decrease timer to a predetermined unload time;

h) determining a sequence of predetermined breathing gas pressure values for the second portion of the current breathing cycle based at least in part on the first and second predetermined breathing gas pressure values; and i) changing the valve step position based at least in part on the sequence of predetermined breathing gas pressure values until the decrease timer is expired.

60. The method of claim 56 wherein the changing in e) comprises:

f) determining a second predetermined breathing gas pressure value;

g) setting an increase timer to a predetermined load time;

h) determining a sequence of predetermined breathing gas pressure values for the third portion of the current breathing cycle based at least in part on the first and second predetermined breathing gas pressure values;

i) changing the valve step position based at least in part on the sequence of predetermined breathing gas pressure values until the increase timer is expired.

61. A method of providing a breathing gas to a patient comprising:

controlling a valve position to output a first target gas pressure level to the patient during at least a portion of the patient's inhalation breathing state;

monitoring an actual gas pressure level output to the patient;

determining a valve position setting based on the monitored gas pressure level;

determining a valve position setting threshold;

determining at least a second target gas pressure level that is less than the first target gas pressure level;

if the valve position setting falls below the valve position setting threshold, controlling the valve position to output the second target gas pressure level to the patient for a predetermined time period during at least a first portion of the patient's exhalation breathing state; and controlling the valve position to output the first target gas pressure level to the patient after the predetermined time period has expired during at least a second portion of the patient's exhalation breathing state.

62. The method of claim 61 wherein determining a valve position threshold comprises determining a difference between at least a peak valve position and a median valve position and determining a patient breathing rate.

63. The method of claim 61 wherein determining at least a second target gas pressure level that is less than the first target gas pressure level comprises lowering the at least first target pressure by a quantity based at least in part on valve position.

64. The method of claim 61 wherein controlling the valve position to output the second target gas pressure level to the patient for a predetermined time period during at least a first portion of the patient's exhalation breathing state comprising outputting at least the second target gas pressure level at the onset of exhalation for a predetermined time period.

65. The method of claim 61 wherein controlling the valve position to output the second target gas pressure level to the patient for a predetermined time period during at least a first portion of the patient's exhalation breathing state comprises determining a plurality of decrease target gas pressure levels between the first target gas pressure level and the second target gas pressure level.

66. The method of claim 61 wherein controlling the valve position to output the first target gas pressure level to the patient after the predetermined time period has expired comprises determining a plurality of increase target gas pressure levels between the second target gas pressure level and the first target gas pressure level.

67. The method of claim 61 wherein determining a valve position setting based on the monitored gas pressure level comprises comparing the first target gas pressure level to the monitored gas pressure level.

* * * * *

UNITED STATES PATENT AND TRADEMARK OFFICE
CERTIFICATE OF CORRECTION

PATENT NO. : 7,621,270 B2  
APPLICATION NO. : 11/157089  
DATED : November 24, 2009  
INVENTOR(S) : Morris et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1187 days.

Signed and Sealed this

Twenty-sixth Day of October, 2010

David J. Kappos  
*Director of the United States Patent and Trademark Office*